United States Patent
Murayama et al.

[11] Patent Number: 5,863,945
[45] Date of Patent: Jan. 26, 1999

[54] AMIDE DERIVATIVES AND EXTERNAL SKIN OR HAIR CARE PREPARATIONS

[75] Inventors: Koichi Murayama, Wakayama; Masahide Hoshino, Tochigi; Hiroshi Kusuoku, Tochigi; Minoru Nagai, Tochigi; Kiyoko Sugino, Tokyo, all of Japan

[73] Assignee: Kao Corporation, Tokyo, Japan

[21] Appl. No.: 952,110

[22] PCT Filed: May 16, 1996

[86] PCT No.: PCT/JP96/01298

§ 371 Date: Nov. 24, 1997

§ 102(e) Date: Nov. 24, 1997

[87] PCT Pub. No.: WO96/37462

PCT Pub. Date: Nov. 28, 1996

[30] Foreign Application Priority Data

May 24, 1995 [JP] Japan ................................ 7-124825

[51] Int. Cl.⁶ ............... A61K 31/195; C07C 235/06; C07C 233/05
[52] U.S. Cl. ................. 514/563; 514/629; 554/64; 554/66; 564/224
[58] Field of Search .................. 514/563, 629; 554/64, 66; 564/224

[56] References Cited

FOREIGN PATENT DOCUMENTS

| | | |
|---|---|---|
| 0227994 | 7/1987 | European Pat. Off. . |
| 0282816 | 3/1988 | European Pat. Off. . |
| 0596450 | 5/1994 | European Pat. Off. . |
| 0398272 | 5/1998 | European Pat. Off. . |
| 64-31752 | 2/1989 | Japan . |

*Primary Examiner*—Shailendra Kumar
*Attorney, Agent, or Firm*—Oblon, Spivak, McClelland, Maier & Neustadt, P.C.

[57] ABSTRACT

This invention relates to amide derivatives represented by the following formula (1), amide derivative synthesis intermediates represented by the following formula (2), (3) or (4), and external skin care preparations, cosmetic hair care formulations and bath medicines containing the amide derivatives (1):

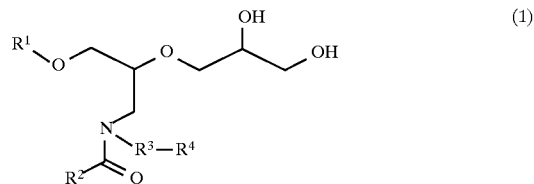

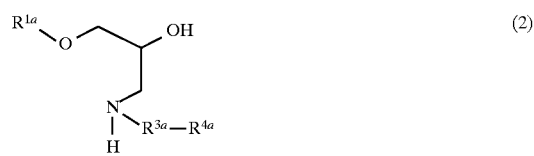

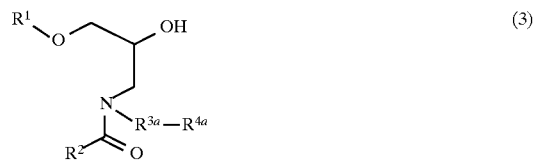

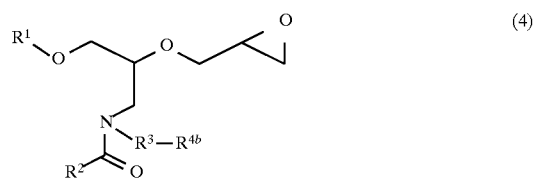

wherein $R^1$ and $R^{1a}$ are, for example, tetradecyl or hexadecyl, $R^2$ is, for example, tridecyl or pentadecyl, $R^3$ is, for example, ethylene or trimethylene, $R^{3a}$ is, for example, trimethylene, and $R^4$, $R^{4a}$ and $R^{4b}$ are, for example, methoxy or ethoxy. When added to external skin care preparations, bath medicines and cosmetic hair care formulations, the amide derivatives (1) exhibit advantageous effects such as skin-roughness preventing/curing effects and hair touch-feeling improving effects.

10 Claims, No Drawings

AMIDE DERIVATIVES AND EXTERNAL SKIN OR HAIR CARE PREPARATIONS

This application is a continuation of PCT/JP96/01298, filed May 16, 1996.

TECHNICAL FIELD

This invention relates to amide derivatives which can enhance water-retaining ability of the horny layer of the skin, are excellent in skin-roughness lessening effects and have good compatibility and low interaction with various cosmetic bases. This invention is also concerned with synthesis intermediates for the amide derivatives and further, with external skin care preparations, cosmetic hair care formulations and bath medicines containing the amide derivatives.

BACKGROUND ART

To keep the skin moisturized and soft, water in the horny layer is known to be important. Maintenance of availability of such water is considered to rely upon water-soluble components contained in the horny layer, namely, free amino acids, organic acids, urea or inorganic ions.

With the foregoing in view, it has been strived to lessen or prevent skin roughness by adding such substances either singly or in combination in medicinal external skin care preparations or cosmetics.

Besides the substances mentioned above, numerous humectants having high affinity with water have been developed and are used for lessening skin roughness.

However, when such humectants are applied to the skin, they remain on the skin horny layer and act to supply water to keratin. Moreover, their effects are temporary. They cannot therefore be considered to fundamentally improve the water-retaining ability of the horny layer and to basically prevent or cure skin roughness.

As an external skin care preparation effective in basically improving the water-retaining ability of the horny layer, the present assignee already proposed an external skin care preparation comprising an amide derivative represented by the following formula (5) (Japanese Patent Laid-Open No. 228048/1987, now Japanese Patent Publication No. 42934/1989):

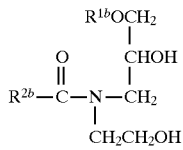

(5)

wherein $R^{1b}$ represents a linear or branched, saturated or unsaturated hydrocarbon group having 10 to 26 carbon atoms and $R^{2b}$ represents a linear or branched, saturated or unsaturated hydrocarbon group having 9 to 25 carbon atoms.

Further, the present assignee also proposed external skin care preparations comprising amide derivatives having similar effects inter alia in Japanese Patent Laid-Open Nos. 216812/1988, 218609/1988, 222107/1988, 227513/1988, 29347/1989 and 31752/1989.

Moreover, the present assignee found that cosmetic hair care formulations containing amide derivatives represented by the below-described formula (6) can penetrate into the hair to effectively protect the same, can prevent chlorosis of the skull and can improve the touch-feeling of the hair, and also proposed them in Japanese Patent Laid-Open No. 9913/1989.

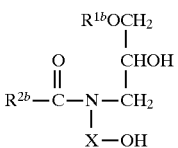

(6)

wherein $R^{1b}$ represents a linear or branched, saturated or unsaturated hydrocarbon group having 10 to 26 carbon atoms, $R^{2b}$ represents a linear or branched, saturated or unsaturated hydrocarbon group having 9 to 25 carbon atoms, and X represents $-(CH_2)_n-$ in which n stands for an integer of 2 to 6.

Although these amide derivatives bring about the above-described excellent advantageous effects, they have properties such as a high melting point, high crystallinity and low solubility in bases so that when added to external skin care preparations and cosmetic hair care formulations, they still involve unsolved problems in compatibility, interaction and the like.

DISCLOSURE OF THE INVENTION

An object of the present invention is therefore to provide an amide derivative effective in fundamentally improving (maintaining and enhancing) the water-retaining ability of the horny layer and, when added to an external skin care preparation or cosmetic hair care formulation, capable of exhibiting improved compatibility and reduced interaction owing to improvements such as reductions in melting point and crystallinity and an improvement in the solubility in a base; an external skin care preparation comprising the amide derivative and, when applied to the skin, being capable of improving the water-retaining ability of the horny layer, preventing or curing skin roughness or inflammation, and also preventing aging of the skin; a cosmetic hair care formulation comprising the amide derivative, having excellent ability for protecting and maintaining the hair and skull and capable of improving the touch feeling of hair; and a bath medicine comprising the amide derivative and providing excellent bathing effects.

As a result of extensive research, the present inventors found that a novel amide derivative represented by the following formula (1) and an external skin care preparation, cosmetic hair care preparation and bath medicine comprising the amide derivative can achieve the above-described object, leading to the completion of the present invention.

In one aspect of the present invention, there is thus provided an amide derivative represented by the following formula (1):

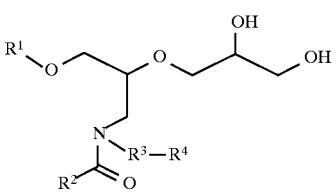

(1)

wherein $R^1$ and $R^2$ may be the same or different and individually represent an optionally-hydroxylated hydrocarbon group having 1 to 40 carbon atoms, $R^3$ represents a linear or branched alkylene group having 1 to 6 carbon atoms or a single bond, and $R^4$ represents a hydrogen atom, a linear or branched alkoxyl group having 1 to 12 carbon atoms or a 2,3-dihydroxypropyloxy group, with the proviso that $R^4$ is a hydrogen atom when $R^3$ is a single bond.

In another aspect of the present invention, there is also provided an amine derivative represented by the following formula (2):

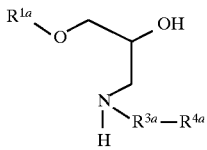

wherein $R^{1a}$ represents an optionally-hydroxylated hydrocarbon group having 4 to 40 carbon atoms, $R^{3a}$ represents a linear or branched alkylene group having 3 to 6 carbon atoms, and $R^{4a}$ represents a linear or branched alkoxyl group having 1 to 12 carbon atoms. This amine derivative (2) is useful as a synthesis intermediate for the amide derivative (1).

In a further aspect of the present invention, there is also provided an amide derivative represented by the following formula (3):

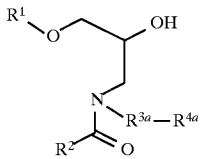

wherein $R^1$ and $R^2$, $R^{3a}$ and $R^{4a}$ represent the same groups as defined above. This amide derivative (3) is useful as a synthesis intermediate for the amide derivative (1).

In a still further aspect of the present invention, there is also provided an amide derivative represented by the following formula (4):

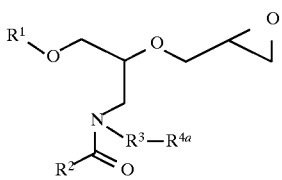

wherein $R^1$ and $R^2$ may be the same or different and individually represent an optionally-hydroxylated hydrocarbon group having 1 to 40 carbon atoms, $R^3$ represents a linear or branched alkylene group having 1 to 6 carbon atoms or a single bond, and $R^{4b}$ represents a hydrogen atom, a linear or branched alkoxyl group having 1 to 12 carbon atoms or a 2,3-epoxypropyloxy group, with the proviso that $R^{4b}$ is a hydrogen atom when $R^3$ is a single bond. This amide derivative (4) is useful as a synthesis intermediate for the amide derivative (1).

In still further aspects of the present invention, there are also provided an external skin care preparation, a cosmetic hair care formulation and a bath medicine, all of which comprise the amide derivative (1).

In a still further aspect of the present invention, there is also provided a skin or hair care method which comprises applying to the skin or hair a preparation or formulation comprising the amide derivative (1).

In a still further aspect of the present invention, there is also provided a bathing method which comprises dissolving or dispersing the amide derivative (1).

In a still further aspect of the present invention, there is also provided use of the amide derivative (1) as an external skin care preparation, a cosmetic hair care formulation or a bath medicine.

The amide derivative according to the present invention has excellent water-retaining ability and water-shielding ability and is highly effective for improving the water-retaining ability of the horny layer of the skin. Further, owing to improvements such as reductions in melting point and crystallinity and an improvement in the solubility in various bases, the amide derivative has good compatibility and low interaction with the various cosmetic bases. The external skin care preparation added with the amide derivative according to the present invention can prevent and cure skin roughness or inflammation and can also show effects for the prevention of aging of the skin. In addition, the cosmetic hair care formulation added with the amide derivative has excellent ability to protect and maintain the hair and skull, thereby making it possible to improve the touch feeling of the hair.

BEST MODE FOR CARRYING OUT THE INVENTION:

In the amide derivative (1) according to the present invention, $R^1$ and $R^2$ may be the same or different and individually represent a linear or branched, saturated or unsaturated, optionally-hydroxylated hydrocarbon group having 1 to 40 carbon atoms. Examples of $R^1$ and $R^2$ include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, heneicosyl, docosyl, nonacosyl, triacontyl, isostearyl, isoheptadecyl, 2-ethylhexyl, 1-ethylheptyl, 8-heptadecyl, 8-heptadecenyl, 8,11-heptadecadienyl, 2-heptylundecyl, 9-octadecenyl, 1-hydroxynonyl, 1-hydroxypentadecyl, 2-hydroxypentadecyl, 15-hydroxypentadecyl, 11-hydroxyheptadecyl, and 11-hydroxy-8-heptadecenyl.

Preferred as $R^1$ is a linear or branched, alkyl or alkenyl group having 8 to 26 carbon atoms. Examples include octyl, decyl, dodecyl, tetradecyl, hexadecyl, octadecyl, docosyl, triacontyl, isostearyl, 2-ethylhexyl, 2-heptylundecyl and 9-octadecenyl. A hydrocarbon group particularly preferred as $R^1$ is a linear or branched alkyl group having 12 to 22 carbon atoms. Examples include dodecyl, tetradecyl, hexadecyl, octadecyl, docosyl and methyl-branched isostearyl.

Preferred as $R^2$ is a linear or branched, alkyl or alkenyl group having 9 to 25 carbon atoms. Examples include nonyl, undecyl, tridecyl, pentadecyl, heptadecyl, heneicosyl, nonacosyl, isoheptadecyl, 1-ethylheptyl, 8-heptadecyl, 8-heptadecenyl, 8,11-heptadecadienyl, 1-hydroxynonyl, 1-hydroxypentadecyl, 2-hydroxypentadecyl, 1-hydroxypentadecyl, 2-hydroxypentadecyl, 15-hydroxypentadecyl, 11-hydroxyheptadecyl, and 11-hydroxy-8-heptadecenyl. A hydrocarbon group particularly preferred as $R^2$ is a linear or branched alkyl group having 11 to 21 carbon atoms. Examples include undecyl, tridecyl, pentadecyl, heptadecyl, heneicosyl and methyl-branched isoheptadecyl.

$R^3$ represents a linear or branched alkylene group having 1 to 6 carbon atoms or a single bond. Illustrative alkylene groups include methylene, ethylene, trimethylene, tetramethylene, pentamethylene, hexamethylene, 1-methylethylene, 1-methyltrimethylene, 2-methyltrimethylene, 1,1-dimethylethylene, 1-ethylethylene, 1-methyltetramethylene, and 2-ethyltrimethylene. Preferred as $R^3$ is a linear alkylene group having 1 to 6 carbon atoms. Particularly preferred examples are methylene, ethylene and trimethylene.

$R^4$ represents a hydrogen atom, a linear or branched alkoxyl group having 1 to 12 carbon atoms or a 2,3-dihydroxypropyloxy group. Illustrative alkoxyl groups include methoxy, ethoxy, propoxy, butoxy, hexyloxy, octyloxy, decyloxy, 1-methylethoxy, and 2-ethylhexyloxy. Preferred as $R^4$ is a hydrogen atom, a linear or branched alkoxyl group having 1 to 8 carbon atoms or a 2,3-dihydroxypropyloxy group. Particularly preferred examples are H, methoxy, ethoxy, propoxy, butoxy, 1-methylethoxy, 2-ethylhexyloxy and 2,3-dihydroxypropyloxy.

When the amide derivative (1) according to the present invention is added to an external skin care preparation, a cosmetic hair care formulation or a bath medicine, particularly preferred compounds are those having the formula (1) in which $R^1$, $R^2$, $R^3$ and $R^4$ are those selected in combination from the above-described particularly preferred ranges. Particularly preferred is an amide compound of the formula (1) in which $R^1$ is a hexadecyl group, $R^2$ is a tridecyl group, $R^3$ is a trimethylene group, and $R^4$ is a methoxy group, namely, an amide compound represented by the following formula (1a):

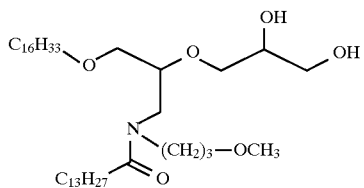

In the amine derivative (2) according to the present invention, examples of $R^{1a}$ are similar to the groups of $R^1$ in the amide derivative (1) except for the omission of methyl, ethyl and propyl. Preferred examples of $R^{1a}$ are similar to those of $R^1$. Examples of $R^{3a}$ are similar to the alkylene groups exemplified as $R^3$ in the amide derivative (1) except for the omission of methylene and ethylene. Preferred as $R^{3a}$ are linear alkylene groups having 3 to 6 carbon atoms, with trimethylene being particularly preferred. Examples of $R^{4a}$ are similar to the groups of $R^1$ in the amide derivative (1). Preferred examples of $R^{4a}$ are similar to those of $R^1$.

In the amide derivative (3) according to the present invention, $R^1$, $R^2$, $R^{3a}$ and $R^{4a}$ have the same meanings as defined above and their preferred examples are similar to those exemplified above.

In the amide derivative (4) according to the present invention, $R^1$, $R^2$ and $R^3$ have the same meanings as defined above. $R^{4b}$ represents a hydrogen atom, a linear or branched alkoxyl group having 1 to 12 carbon atoms or a 2,3-epoxypropyloxy group. Specific examples of $R^1$, $R^2$ and $R^3$ are similar to those exemplified above with respect to the amide derivative (1). Their preferred examples are similar to the preferred examples mentioned above. Examples of the linear or branched alkoxyl group having 1 to 12 carbon atoms as $R^{4b}$ are similar to those of $R^4$ in the amide derivative (1). Specifically, a hydrogen atom, alkoxyl groups similar to those exemplified above as $R^4$ and a 2,3-epoxypropyloxy group are preferred.

The amide derivative (1) according to the present invention can be obtained, for example, by the following Preparation Process 1 or Preparation Process 2.

Preparation Process I

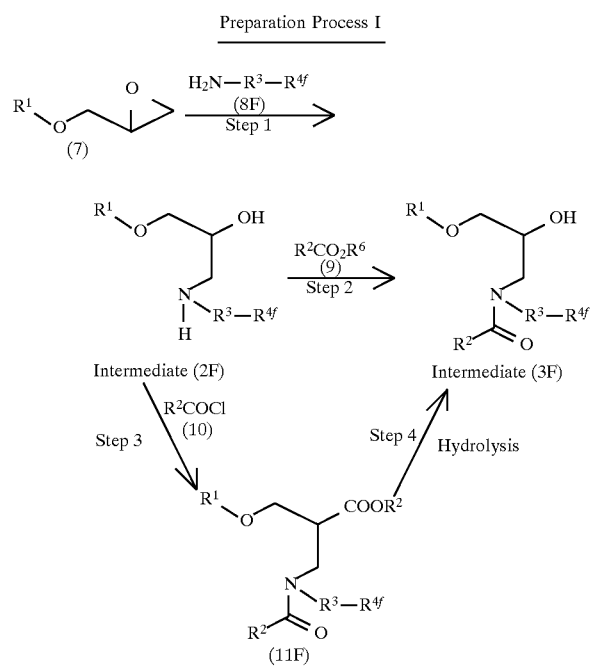

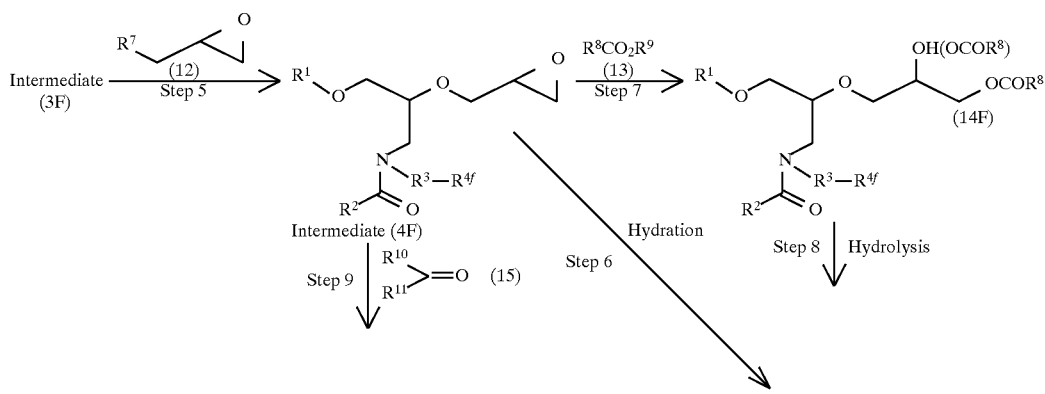

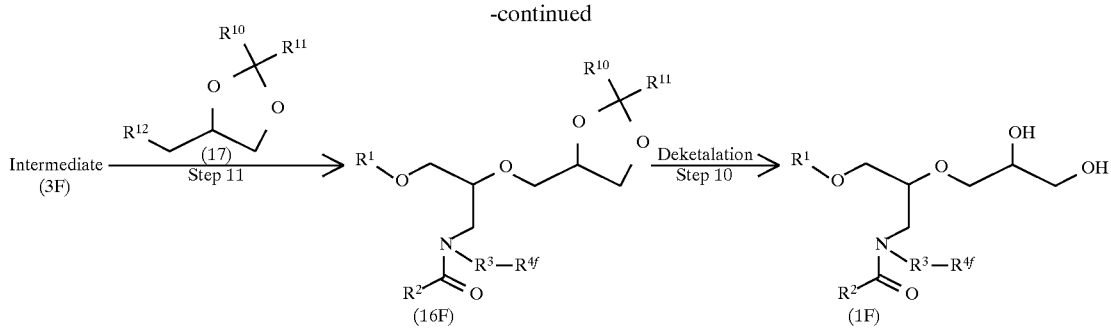

wherein $R^1$, $R^2$ and $R^3$ have the same meanings as defined above, and $R^{4f}$ represents a hydrogen atom or a linear or branched alkoxyl group having 1 to 12 carbon atoms, with the proviso that $R^{4f}$ is a hydrogen atom when $R^3$ is a single bond. $R^6$, $R^8$, $R^{10}$ and $R^{11}$ individually represent a linear or branched, saturated or unsaturated hydrocarbon group having 1 to 8 carbon atoms, with a linear or branched alkyl group having 1 to 5 carbon atoms being preferred and with a methyl group being particularly preferred. $R^9$ represents a hydrogen atom, an alkali metal or a $COR^8$ group, and $R^7$ and $R^{12}$ individually represent an eliminative atom or group such as a halogen atom, mesylate group or tosylate group. From the standpoint of availability and the like, $R^7$ is preferably a chlorine atom or bromine atom, with a chlorine atom being particularly preferred. From the standpoint of availability and the like, $R^{12}$ is preferably a mesylate group or tosylate group.

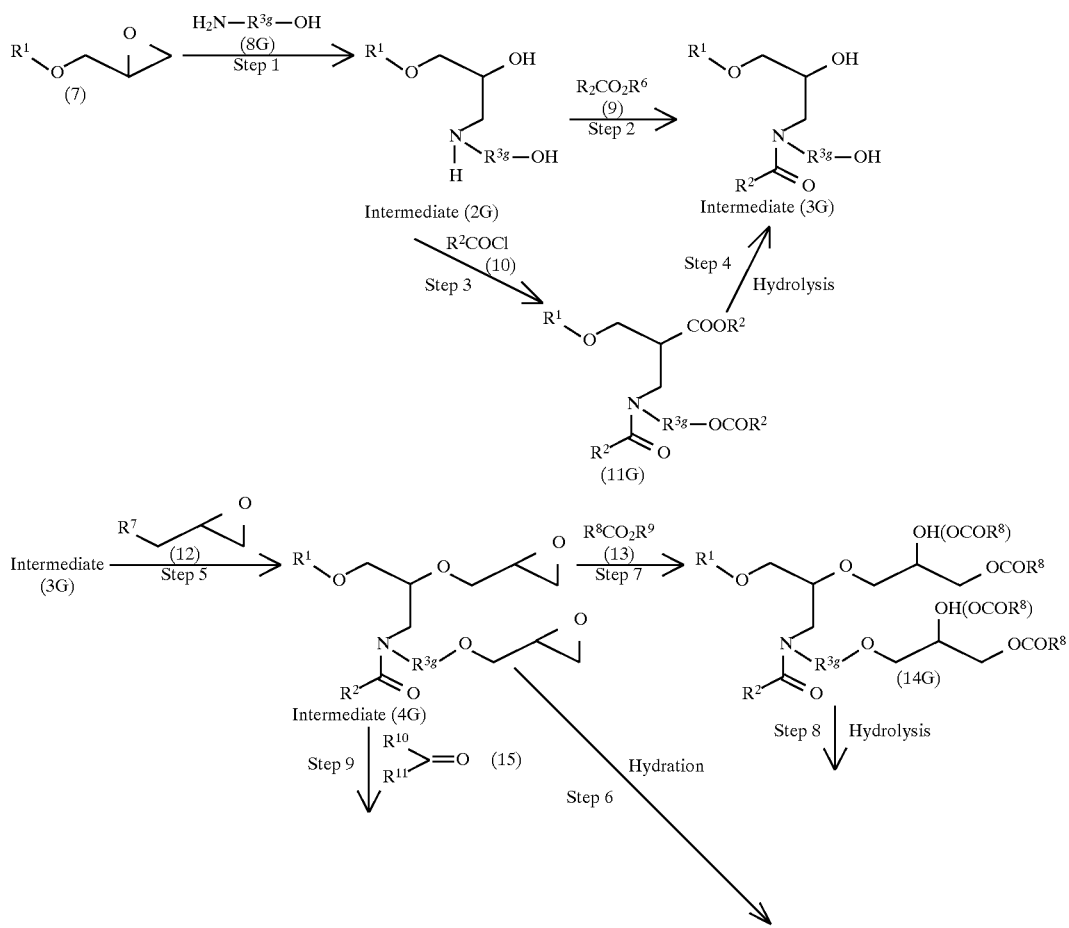

-continued
Preparation Process 2

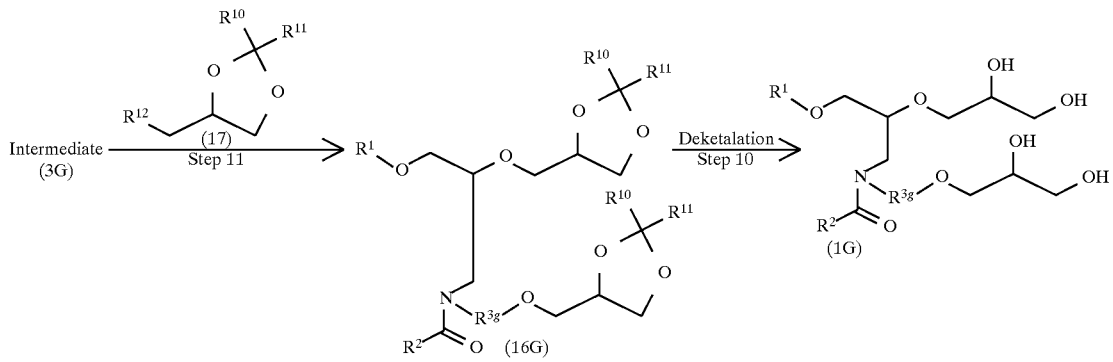

wherein $R^1$, $R^2$ and $R^6$ to $R^{12}$ have the same meanings as defined above, and $R^{3g}$ represents a linear or branched alkylene group having 1 to 6 carbon atoms.

Reaction conditions for the individual steps of the Preparation Process 1 and Preparation process 2 are as follows:

Step 1)

An amino alcohol derivative (2F) or (2G) can be prepared by reacting a glycidyl ether (7) and an amine (8F) or (8G) at room temperature to 150° C. either in a solventless manner or in the presence of water, a lower alcohol such as methanol, ethanol or isopropanol, an ether solvent such as tetrahydrofuran, dioxane or ethylene glycol dimethyl ether, or a mixed solvent of desired two or more solvents thereof.

Step 2)

A amide derivative (3F) or (3G) can be prepared by reacting the amino alcohol derivative (2F) or (2G) with a fatty acid ester (9), preferably a lower alkyl ester of a fatty acid such as the methyl ester or a fatty acid or the ethyl ester of a fatty acid under a reduced pressure of from normal pressure to 0.01 mmHg at room temperature to 150° C. in the presence of a basic catalyst, for example, an alkali metal hydroxide such as potassium hydroxide or sodium hydroxide, an alkaline earth metal hydroxide such as calcium hydroxide, or an alkali metal alcoholate such as sodium methoxide, sodium ethoxide or potassium tert-butoxide. Here, the basic catalyst may be used preferably in an amount of 0.01 to 0.2 equivalent based on the amino alcohol derivative (2F) or (2G). It is preferred to conduct the reaction while taking the resulting alcohol out of the system, as the reaction is allowed to proceed at a higher velocity.

Step 3)

The amide derivative (3F) or (3G) can also be prepared by reacting the amino alcohol derivative (2F) or (2G) with a fatty acid chloride (10) at room temperature to 100° C. either in a solventless manner or in a halogenated hydrocarbon solvent such as chloroform, methylene chloride or 1,2-dichloroethane, an ether solvent such as tetrahydrofuran, dioxane or ethylene glycol dimethyl ether, a hydrocarbon solvent such as hexane, benzene, toluene or xylene or in a mixed solvent of desired two or more solvents thereof in the presence or absence of a base, for example, a tertiary amine such as pyridine or triethylamine to convert the amino alcohol derivative (2F) or (2G) into an amide ester derivative (11F) or (11G) and then, Step 4)

by selectively hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 5)

An amide derivative (4F) or (4G) can be prepared by reacting the amide derivative (3F) or (3G) with 1 to 20 equivalents of an epoxide (12), preferably epichlorohydrin either in a solventless manner or in water, an ether solvent such as tetrahydrofuran, dioxane or ethylene glycol dimethyl ether, a hydrocarbon solvent such as hexane, benzene, toluene or xylene or a mixed solvent of desired two or more solvents thereof in the presence of 1 to 10 equivalents of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate. From the standpoint of its yield and the like, it is preferred to conduct the reaction in the presence of a phase transfer catalyst, for example, a tertiary ammonium salt such as tetrabutylammonium bromide, tetrabutylammonium chloride, hexadecyltrimethylammonium chloride, hexadecyltrimethylammonium bromide, stearyltrimethylammonium chloride or bistetraoxyethylenestearylmethylammonium chloride, or a betaine such as lauryldimethylcarboxyammonium betaine.

Step 6)

An amide derivative (1F) or (1G) can be prepared by hydrating the amide derivative (4F) or (4G) at room temperature to 300° C. under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate, under acidic conditions, for example, in the presence of a mineral acid such as sulfuric acid or hydrochloric acid, a Lewis acid such as boron trifluoride or tin tetrachloride, a carboxylic acid such as acetic acid, tetradecanoic acid or hexadecanoic acid or a sulfonic acid such as p-toluenesulfonic acid, or under mixed base-acid conditions.

Step 7)

The amide derivative (1F) or (1G) can also be prepared by reacting the amide derivative (4F) or (4G) with one or more carboxylic acid derivatives (13), preferably lower fatty acids such as acetic acid, alkali metal salts of lower fatty acids such as sodium acetate, lower fatty acid anhydrides such as acetic anhydride either singly or in combination in the presence or absence of a basic catalyst, for example, a tertiary amine such as triethylamine to convert the amide derivative (4F) or (4G) into an ester-amide derivative (14F) or (14G) and then, Step 8)

by selectively hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 9)

The amide derivative (1F) or (1G) can also be prepared by reacting the amide derivative (4F) or (4G) with a carbonyl compound (15), preferably a lower fatty acid ketone such as acetone or methyl ethyl ketone in the presence of an acid catalyst, for example, a mineral acid such as sulfuric acid, hydrochloric acid or phosphoric acid, a carboxylic acid such as acetic acid, or Lewis acid such as boron trifluoride or tin tetrachloride to convert the amide derivative (4F) or (4G) into a 1,3-dioxolane-amide derivative (16F) or (16G) and then, Step 10)

by subjecting the a 1,3-dioxolane-amide derivative (16F) or (16G) to deketalation under acidic conditions, for example, in the presence of a mineral acid such as sulfuric acid, hydrochloric acid or phosphoric acid, a carboxylic acid such as acetic acid or a sulfonic acid such as p-toluenesulfonic acid.

Step 11)

The 1,3-dioxolane-amide derivative (16F) or (16G) can also be prepared by reacting the amide derivative (3F) or (3G) with a glycerol derivative (17) in the presence of a base, for example, an alkali metal hydroxide such as potassium hydroxide or sodium hydroxide, an alkaline earth metal hydroxide such as potassium hydroxide, an alkali metal carbonate such as potassium carbonate, an alkaline earth metal carbonate such as calcium carbonate or an alkali metal hydride such as sodium hydride either in a solventless manner or in an aprotonic polar solvent such as N,N-dimethylformamide or dimethylsulfoxide, an ether solvent such as tetrahydrofuran, dioxane or ethylene glycol dimethyl ether, a hydrocarbon solvent such as hexane, benzene, toluene or xylene, or a mixed solvent of desired two or more solvents thereof.

The amide derivative (1) according to the present invention, which has been obtained as described above, can be purified by a method known per se in the art. When adding the amide derivative (1) to external skin care preparations and cosmetic hair care formulations, the amide derivative (1) can be used either in the form of a compound purified to 100% purity or in the form of a mixture of a purity of 70% or higher but lower than 100% containing one or more intermediates and/or one or more reaction byproducts while assuring excellent effects and performance without safety problems. It is to be noted that the compound according to the present invention include its solvates typified by its hydrate.

Examples of amide derivatives according to the present invention, which can be obtained following the Preparation Process 1, include the following compounds:

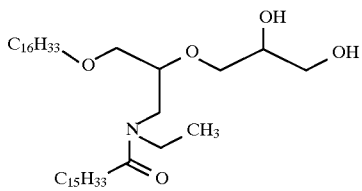

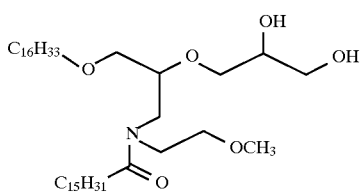

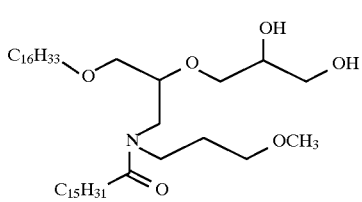

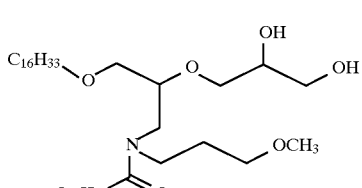

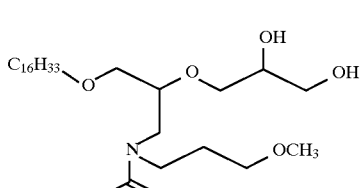

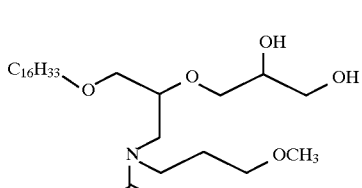

($R^2 = C_{17}H_{35} + C_{15}H_{31} + C_{13}H_{27}$)

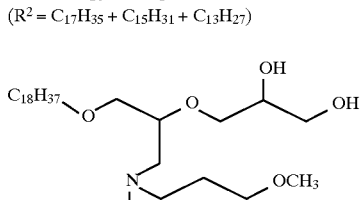

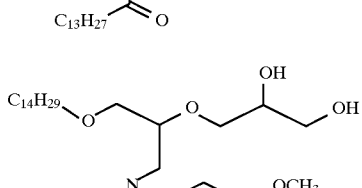

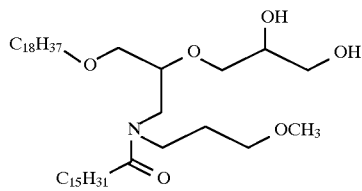

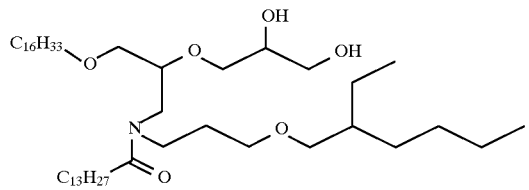

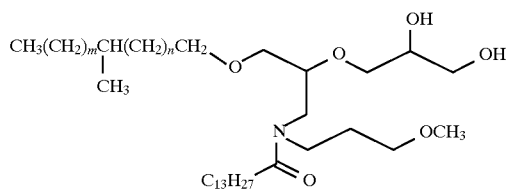

wherein m and n represent numerals having distributions centered at m=7 and n=7 with m+n in a range of from 10 to 16, m in a range of from 4 to 10 and n in a range of from 4 to 10.

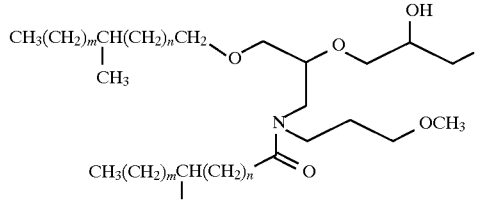

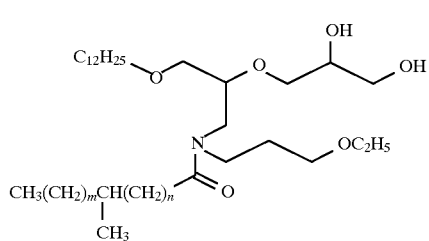

wherein m and n have the same meanings as defined above.

wherein m and n have the same meanings as defined above.

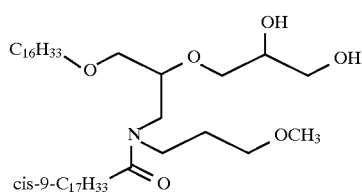

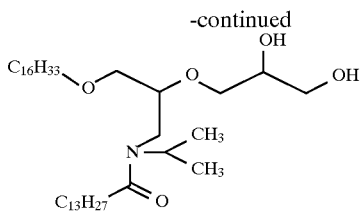

Examples of amide derivatives according to the present invention, which can be obtained following the Preparation Process 2, include the following compounds:

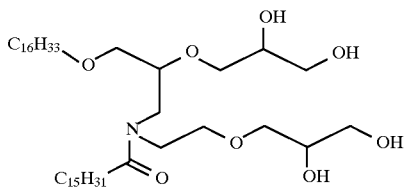

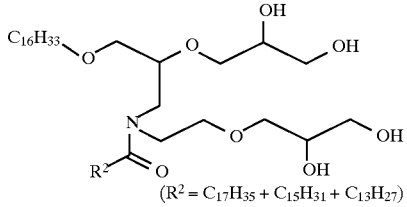

($R^2 = C_{17}H_{35} + C_{15}H_{31} + C_{13}H_{27}$)

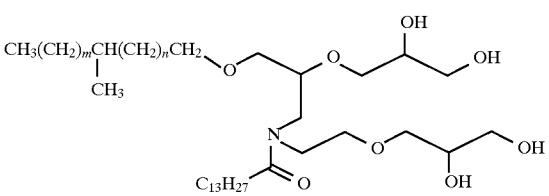

wherein m and n represent numerals having distributions centered at m=7 and n=7 with m+n in a range of from 10 to 16, m in a range of from 4 to 10 and n in a range of from 4 to 10.

No particular limitation is imposed on the amount of the amide derivative (1) to be added to the external skin care preparation according to the present invention. However, in the case of an emulsion-type external skin care preparation, the amide derivative can be added generally in an amount of 0.001 to 50 wt. % (hereinafter referred to merely as "%") based on the whole composition, with 0.1 to 20% being preferred. On the other hand, in the case of an oil-base external skin care preparation containing a liquid hydrocarbon such as squalane as a base, the amide derivative can be added generally in an amount of 1 to 50%, with 1 to 20% being particularly preferred. In the case of a bath medicine, the amide derivative can be added generally in an amount of 0.001 to 50%, with 0.1 to 20% being especially preferred.

It is preferred to use a surfactant in combination with the external skin care preparation according to the present invention. As the surfactant, a nonionic surfactant, anionic surfactant or amphoteric surfactant can each be used, with a nonionic surfactant being particularly preferred.

Examples of the nonionic surfactant include polyoxyethylene alkyl ethers, polyoxyethylene alkylphenyl ethers, polyoxyethylene fatty acid esters, sorbitan fatty acid esters, polyoxyethylene sorbitan fatty acid esters, fatty acid monoglycerides, and glyceryl ethers. Of these, preferred examples are glyceryl ethers represented by the following formula (18):

$$R^{20}-OCH_2-\underset{OH}{CH}-CH_2OH \quad (18)$$

wherein $R^{20}$ represent alkyl groups having 8 to 24 carbon atoms, with those in which $R^{20}$ is represented by the following formula (19):

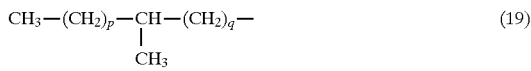
$$CH_3-(CH_2)_p-\underset{CH_3}{CH}-(CH_2)_q- \quad (19)$$

wherein p stands for integers of 4 to 10, q stands for integers of 5 to 11, p+q ranges from 11 to 17, and q has distributions centered at q=8 being particularly preferred.

The surfactant can be added in an amount of 0.1 to 20%, especially 0.1 to 5% based on the whole composition.

External skin care preparations according to the present invention can be classified roughly into medicinal external skin care preparations and cosmetics depending on the manners of their use.

Examples of medicinal external skin care preparations include various ointments each of which contains one or more medicinally-effective ingredients. The ointments can be either those containing an oily base as a base or those containing an oil/water or water/oil emulsion base as a base. No particular limitation is imposed on the oily base. Usable examples include vegetable oils, animal oils, synthetic oils, fatty acids, and natural or synthetic glycerides. With respect to the medicinally-effective ingredients, no specific limitation is imposed either. For example, analgesic and antiphlogistic agents, antipuritics, disinfectants, astringents, emollients, hormones and the like can be selectively employed as needed.

When employed as cosmetics, it is possible to add, besides essential ingredients, other ingredients conventionally employed as ingredients of cosmetics, for example, oils, humectants, ultraviolet absorbers, alcohols, chelating agents, pH regulators, antiseptics, thickeners, colors, perfumes, plant extracts and the like in combinations as desired.

Cosmetics can be formulated into various forms, for example, cosmetic skin care formulations such as water/oil or oil/water emulsion cosmetics, creams, cosmetic emulsions, toilet waters, oil-base cosmetics, lipsticks, foundations, and skin-cleansing formulations.

No particular limitation is imposed on the amount of the amide derivative (1) to be added to the cosmetic hair care formulation according to the present invention. However, in the case of a shampoo or the like, the amide derivative (1) can be added preferably in an amount of about 0.001 to 5%. In the case of a rinse, a treatment, a conditioner or the like, the amide derivative can be added preferably in an amount of about 0.1 to 20%. In the case of a hair liquid, a hair tonic or the like, the amide derivative can be added preferably in an amount of about 0.01 to 5%.

Examples of surfactants—which can be added when the cosmetic hair care formulation according to the present invention is a shampoo, a hair rinse, a hair conditioner, a hair treatment or the like—include anionic surfactants, amphoteric surfactants, nonionic surfactants and cationic surfactants. Illustrative anionic surfactants include linear or branched alkylbenzenesulfonate salts, linear or branched alkyl or alkenyl ether sulfate salts, alkyl- or alkenyl-containing alkyl or alkenylsulfate salts, olefinsulfonate salts, alkanesulfonate salts, unsaturated fatty acid salts, alkyl or alkenyl ether carboxylate salts, alkyl- or alkenyl-containing α-sulfofatty acid salts or esters, N-acylamino acid surfactants containing one or more acyl group or free carboxylic acid residual groups, and phosphate mono or diester surfactants containing one or more alkyl groups or alkenyl groups.

Illustrative amphoteric surfactants include alkyl-, alkenyl- or acyl-containing imidazoline amphoteric surfactants, carbobetaine amphoteric surfactants, amidobetaine amphoteric surfactants, sulfobetaine amphoteric surfactants, hydrosulfobetaine amphoteric surfactants, and amidosulfobetaine amphoteric surfactants.

Illustrative nonionic surfactants include polyoxyethylene alkyl or alkenyl ethers, polyoxyethylene alkyl phenyl ethers, polyoxypropylene alkyl or alkenyl ethers, polyoxybutylene alkyl or alkenyl ethers, ethylene oxide-propylene oxide or ethylene oxide-butylene oxide adduct nonionic surfactants, higher fatty acid alkanolamides and their alkylene oxide adducts, sucrose fatty acid esters, fatty acid glycerin monoesters, and alkylamine oxides.

Illustrative cationic surfactants include mono or di-long chain alkyl quaternary ammonium salts.

Examples of counter ions of anionic residual groups of these surfactants include alkali metal ions such as sodium and potassium ions, alkaline earth metal ions such as calcium and magnesium ions, ammonium ion, and alkanolamine residual groups containing 1 to 3 alkanol groups having 2 to 3 carbon atoms such as monoethanolamine, diethanolamine, triethanolamine and triisopropanolamine residual groups. Examples of counter ions of cationic residual groups include halogen ions such as chlorine, bromine and iodine ions, methosulfate ion and saccharinate ion.

In shampoos or the like, among these surfactants, anionic surfactants such as alkyl ether sulfate salts, alkyl sulfate salts and olefinsulfonate salts are preferred as principal surfactants. Suitable examples include sodium polyoxyethylene lauryl ether sulfate (average number of added ethylene oxide: 2 to 3 moles), lauryl sulfate triethanolamine, and sodium α-olefinsulfonates (average carbon number: 12 to 14).

In a shampoo or the like, these surfactants can be added in a total amount of 5 to 30%, preferably 10 to 20% based on the composition. In a hair rinse, hair treatment, hair conditioner or the like, a nonionic surfactant or cationic surfactant can be added in an amount of 0.1 to 50%, preferably 0.5 to 20% based on the composition.

Where the cosmetic hair care formulation is a hair rinse, hair treatment or hair conditioner, a long-chain alkyl quaternary ammonium salt and an oil or fat scan be additionally incorporated to impart good feeling of touch to the hair. Examples of the long-chain alkyl quaternary ammonium salt include long-chain alkyl quaternary ammonium salts represented by the following formula (20):

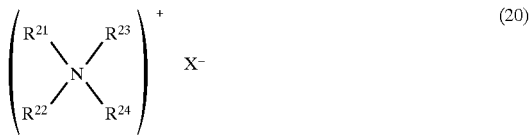

$$\begin{pmatrix} R^{21} & R^{23} \\ \diagdown & \diagup \\ & N & \\ \diagup & \diagdown \\ R^{22} & R^{24} \end{pmatrix}^+ X^- \quad (20)$$

wherein one or two of $R^{21}$ to $R^{24}$ individually represent a linear or branched, long-chain alkyl group having 8 to 24 carbon atoms, the remainders individually represent an alkyl group having 1 to 3 carbon atoms, a hydroxyalkyl group or a benzyl group, and X represents a halogen atom or an alkyl sulfate group having 1 to 2 carbon atoms. These long-chain alkyl quaternary ammonium salts can be used either singly or in combination. Of the above-described long-chain alkyl quaternary ammonium salts represented by the formula (20), those containing branched chains as the long-chain alkyl groups can be synthesized in a manner known per se in the art, using their corresponding branched fatty acids or branched higher alcohols as raw materials. These raw materials can be either naturally occurring substances or synthesized products. Illustrative natural raw materials include lanolin fatty acids such as isoacids and antiisoacids and terpene alcohols such as farnesol. On the other hand, illustrative synthetic raw materials include oxoalcohols obtained from their corresponding olefins as raw materials by the oxo process, Guerbet alcohols obtained from their corresponding alcohols or aldehydes by Guerbet condensation or aldol condensation, and 2-alkylalkanols. In the case of an oxoalcohol, for example, use of an α-olefin as a raw material results in the formation of a higher alcohol having a lower branching rate. On the other hand, use of an internal olefin leads to a higher branching rate while employment of a branched olefin leads to a branching rate of 100%.

In these branched long-chain alkyl quaternary ammonium salts, each branched alkyl group may preferably be a 2-methylalkyl group represented by the following formula (21):

wherein $R^{25}$ represents a linear alkyl group having 5 to 13 carbon atoms. Preferred specific examples include 2-methyloctyl, 2-methyldecyl, 2-methylundecyl, 2-methyldodecyl, 2-methyltridecyl, 2-methyltetradecyl, and 2-methylheptadecyl. These 2-methylalkyl groups are generally derived from their corresponding oxoalcohols. Each of these oxoalcohols is generally obtained as a mixture with a linear alcohol.

Illustrative branched long-chain alkyl quaternary ammonium salts having these branched alkyl groups include alkyltrimethylammonium chlorides, dialkyldimethylammonium chlorides, alkyldimethylbenzylammonium chlorides, alkyltrimethylammonium bromides, alkyltrimethylammonium hydrogensulfates, alkyltrimethylammonium methosulfates, and dialkylmethylhydroxymethylammonium chlorides. Of these, particularly preferred are those having 2-methylalkyl groups represented by the formula (21), for example, branched mono-long-chain alkyl quaternary ammonium salts such as 2-methyldecyltrimethylammonium chloride, 2-methyldodecyltrimethylammonium chloride, 2-methyltetradecylammonium chloride; branched di-long-chain alkyl quaternary ammonium salts such as 2-methyldecylundecyldimethylammonium chloride, 2-methyldodecyltridecyldimethylammonium chloride and 2-methyltetradecylpentadecyldimethylammonium chloride; and branched di-long-chain alkylammonium salts with both the long-chain alkyl groups being branched, such as di(2-methyldecyl)dimethylammonium chloride, di(2-methyldodecyl)dimethylammonium chloride and di-(2-methyltetradecyl)dimethylammonium chloride.

Further, illustrative linear long-chain alkyl groups include decyl, undecyl, dodecyl, tridecyl, tetradecyl, pentadecyl, hexadecyl, octadecyl and eicosanyl.

As the oil or fat, it is possible to use an oil or fat which is commonly employed. Examples include liquid paraffins, glycerides, higher alcohols, lanolin derivatives, esters, and higher fatty acids. Preferred usable examples of glycerides include monoglycerides derived from saturated or unsaturated, linear or branched fatty acids having 12 to 24 carbon atoms. Among these oils and fats, particularly preferred are higher alcohols having a linear or branched alkyl or alkenyl group having 12 to 26 carbon atoms. Preferred specific examples include cetyl alcohol, stearyl alcohol, arachic alcohol, behenyl alcohol, carnaubyl alcohol, and ceryl alcohol.

These long-chain alkyl quaternary ammonium salts can be added in an amount of 0.01 to 20%, while these oils or fats can be added in an amount of 0.1 to 30%.

Where the cosmetic hair care formulation is a hair liquid, hair tonic or the like, one or more nonionic surfactants can also be used in combination. As such nonionic surfactants, those described above as examples for addition to the external skin care preparation can be exemplified likewise.

The above nonionic surfactants can be added in a total amount of 0.01 to 20%, especially 0.1 to 5% based on the whole composition.

The cosmetic hair care formulation according to the present invention, which contains the amide derivative (1) added thereto, can be formed, without any limitation, into an application form such as an aqueous solution, ethanol solution, emulsion, suspension, gel, solid, aerosol or powder. Further, it is also possible to add, besides the above-described ingredients, one or more other ingredients similar to those incorporated as cosmetic ingredients in the above-described cosmetic skin care formulations, as needed.

The bath medicine according to the present invention, which contains the amide derivative (1) added thereto, can be formulated into an application form such as a powder, granules, an emulsion or tablets. Further, one or more ingredients which are generally used in bath medicines can be added as desired.

Examples of ingredients usable in the bath medicine include various medicinally-effective ingredients, inorganic salts, perfumes, and plant extracts.

When the bath medicine to which the amide derivative (1) and one or more of such optional ingredients have been added is dissolved or dispersed in water and one bathes in the water, excellent bathing effects can be obtained.

EXAMPLES

The present invention will hereinafter be described on the basis of the following examples. It is however to be borne in mind that the present invention is not limited to or by the following examples. In Examples 1 to 10, the amide derivatives according to the present invention were prepared following the Preparation Process 1 while in Examples 11 and 12, the amide derivatives according to the present invention were prepared following the Preparation Process 2.

Example 1

In a 2-l five-necked flask fitted with a stirrer, a dropping funnel, a nitrogen inlet tube and a distillation equipment, 743.2 g (8.34 mol) of 3-methoxypropylamine and 150 ml of ethanol were charged and, while the resulting mixture was stirred under heat at 80° C. under a nitrogen atmosphere, 165.9 g (0.56 mol) of hexadecyl glycidyl ether were added dropwise to the mixture over 3 hours. After completion of the dropwise addition, the reaction mixture was stirred at 80° C. for 12 hours and the ethanol and excess 3-methoxypropylamine were distilled out under heat and reduced pressure. The residue was purified by chromatography on a silica gel column, whereby 196.5 g of an aminoalcohol derivative (2a) were obtained (yield: 91% based on the hexadecyl glycidyl ether) (step 1).

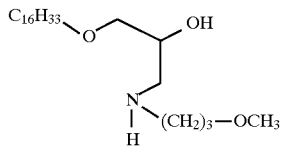

(2a)

The followings are physical properties of the aminoalcohol derivative (2a) so obtained.
White solid.
Melting point: 53° C.
IR($\upsilon_{neat}$,cm$^{-1}$): 3340, 2930, 2855, 1470, 1310, 1120, 1065, 955, 900, 720.
$^1$H-NMR(CDCl$_3$,δ): 0.88 (t,J=6.3 Hz,3 H), 1.25–1.45 (m,26 H), 1.45–1.85 (m,6 H), 2.57–2.76 (m,4 H), 3.32 (s,3 H), 3.38–3.48 (m,6H), 3.77–3.89 (m,1 H).

In a 1-l five-necked flask fitted with a stirrer, a dropping funnel, a nitrogen inlet tube and a distillation equipment, 61.3 g (158.1 mmol) of the compound (2a), which had been obtained above (step 1) and had been molten, and 1.53 g (7.91 mmol) of a 28% methanol solution of sodium methoxide were charged, followed by stirring at 60° C. for 30 minutes under a nitrogen atmosphere. Under the same conditions, 38.3 g (158.1 mmol) of methyl tetradecanoate were added dropwise to the resultant mixture over 1 hour. After completion of the dropwise addition, the reaction mixture was stirred at 60° C. for 5 hours under reduced pressure (80–10 Torr) so that the reaction was brought to completion. The reaction mixture was cooled and then purified by chromatography on a silica gel column, whereby 88.7 g of an amide derivative (3a) were obtained (yield: 94%) (step 2).

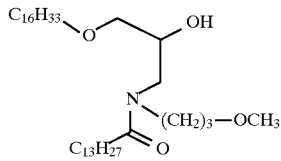

(3a)

The followings are physical properties of the amide derivative (3a) so obtained.
White solid.
Melting point: 48° C.
IR($\upsilon_{neat}$,cm$^{-1}$): 3440, 2930, 2860, 1650, 1625, 1470, 1225, 1210, 1110, 950, 720.
$^1$H-NMR(CDCl$_3$,δ): 0.88 (br t,J=6.3 Hz,6 H), 1.15–1.95 (m,53 H), 2.36 (t, J=7.5 Hz,2 H), 3.29–3.55 (m,10 H), 3.33 (s,3 H), 3.85–3.95 (m,1 H).

In a 1-l five-necked flask fitted with a stirrer, a nitrogen inlet tube and a distillation equipment, 94.5 g (158.0 mmol) of the compound (3a) obtained above (step 2), 1.53 g (4.74 mmol) of tetrabutylammonium bromide, 32.2 g (347.6 mmol) of epichlorohydrin, 12.6 g (315.0 mmol) of sodium hydroxide and 66 ml of toluene were charged, followed by stirring at 45° C. for 10 hours under a nitrogen atmosphere. After the reaction mixture so obtained was washed three times at 70° C. with water, the toluene and excess epichlorohydrin were distilled out under heat and reduced pressure and the residue was purified by chromatography on a silica gel column, whereby 94.9 g of an amide derivative (4a) were obtained (yield: 92%) (step 5).

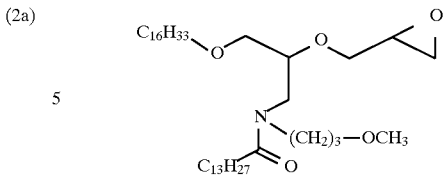

(4a)

The followings are physical properties of the amide derivative (4a) so obtained.
White solid.
Melting point: 38°–39° C.
IR($\upsilon_{neat}$,cm$^{-1}$): 2930, 2855, 1650, 1470, 1425, 1380, 1210, 1120, 905, 840, 720.
$^1$H-NMR(CDCl$_3$,δ): 0.88 (br t,J=6.0 Hz,6 H), 1.10–1.45 (m,46 H), 1.45–1.90 (m,6 H), 2.25–2.48 (m,2 H), 2.50–2.68 (m,1 H), 2.70–2.85 (m,1 H), 3.02–3.20 (m,1 H), 3.20–4.00 (m,13 H), 3.32 (s,3 H).

Into a 100-ml autoclave fitted with a stirrer, 71.3 g (109.0 mmol) of the compound obtained above (step 5), 11.78 g (654.1 mmol) of water, 0.087 g (2.18 mmol) of sodium hydroxide and 0.87 g (4.36 mmol) of tetradecanoic acid were charged, followed by stirring at 160° C. for 6 hours in a closed system. After the reaction mixture was cooled, it was washed twice at 80° C. with a 2% aqueous solution of NaCl and then purified by chromatography on a silica gel column, whereby 68.3 of a target amide derivative (1a) were obtained (yield: 93%) (step 6).

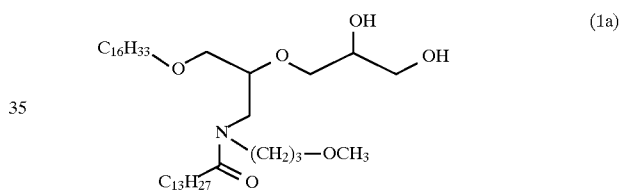

(1a)

The followings are physical properties of the amide derivative (1a) so obtained.
Colorless clear liquid.
IR($\upsilon_{neat}$,cm$^{-1}$): 3445, 2930, 2860, 1630, 1470, 1420, 1380, 1305, 1210, 1120, 720.
$^1$H-NMR(CDCl$_3$,δ): 0.88 (br t,J=6.7 Hz,6 H), 1.15–1.44 (m,46 H), 1.44–1.95 (m,8 H), 2.25–2.45 (m,2 H), 3.20–3.90 (m,16 H), 3.33 (s,3 H).

Into a 500-ml four-necked flask fitted with a stirrer, a nitrogen inlet tube and a distillation equipment, 31.0 g (47.4 mmol) of the compound (4a) obtained above (step 5), 11.9 g (663.7 mmol) of water, 13.6 g (165.9 mmol) of sodium acetate and 104.9 g (1746.8 mmol) of acetic acid were charged, followed by stirring at 70° C. for 19 hours under a nitrogen atmosphere. Excess acetic acid was distilled out under heat and reduced pressure, whereby a mixture containing ester-amide derivatives (14a-1), (14a-2) and (14a-3) were obtained (step 7).

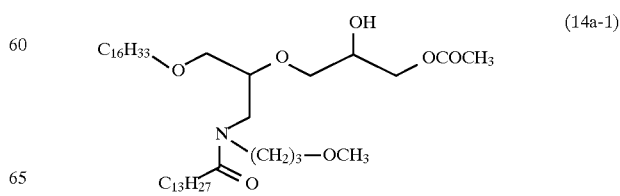

(14a-1)

-continued

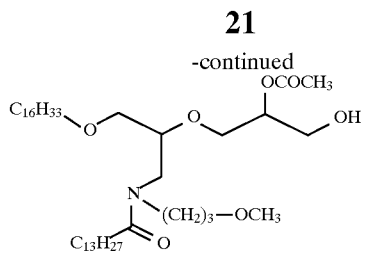

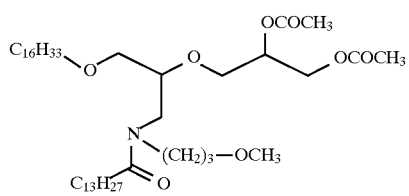

The mixture containing those ester-amide derivatives, without being taken out of the flask, were next added with 59.3 g (711.2 mmol) of a 48% aqueous solution of sodium hydroxide, 18 g of water and 200 ml of butanol, followed by stirring at 80° C. for 3 hours. The butanol was distilled out under heat and reduced pressure. After the residue was diluted in 250 ml of toluene, the resultant solution was washed twice at 70° C with water. The toluene was distilled out under heat and reduced pressure and the residue was purified by chromatography on a silica gel column, whereby 22.3 g of the intended amide derivative (1a) were obtained (yield: 70%) (step 8).

Example 2

Into a 10-l five-necked flask fitted with a stirrer, a dropping funnel, a nitrogen inlet tube and a distillation equipment, 4680 g (52.5 mol) of 3-methoxypropylamine and 900 ml of ethanol were charged and, while the resulting mixture was stirred at 80° C. under heat and a nitrogen atmosphere, 1045 g (3.50 mol) of hexadecyl glycidyl ether were added dropwise to the mixture over 3 hours. After completion of the dropwise addition, the reaction mixture was stirred at 80° C. for 1 hour and the ethanol and excess 3-methoxypropylamine were distilled out under heat and reduced pressure, whereby a product composed of an aminoalcohol derivative (2a) as a principal component was obtained (step 1).

To the product obtained above (step 1), composed of the compound (2a) as the principal component and contained in the 10-l five-necked flask, 9.82 g (0.175 mol) of potassium hydroxide were added. Under ebullation of nitrogen, the resultant mixture was stirred under reduced pressure (60 to 10 Torr) at 80° C. for 3 hours while distilling out the resulting water. With stirring under the same conditions, 882.3 g (3.64 mol) of methyl tetradecanoate were next added dropwise to the reaction mixture over 3 hours. During the dropwise addition, the resulting methanol was distilled out. After completion of the dropwise addition, the mixture was stirred under ebullation of nitrogen and reduced pressure (60 to 10 Torr) at 60° to 45° C. for 10 hours while distilling out the resulting methanol, whereby the reaction was brought to completion and a compound composed of an amide derivative (3a) as a principal component was obtained (step 2).

To the product obtained above (step 2), composed of the compound (3a) as the principal component and contained in the 10-l five-necked flask, 33.9 g (0.105 mol) of tetrabutylammonium bromide, 712.5 (7.70 mol) of epichlorohydrin and 2100 g of toluene were added. Under ebullation of nitrogen, 1750.0 g (21.0 mol) of a 48% aqueous solution of sodium hydroxide were added dropwise under reduced pressure (150 to 50 Torr) at 45° C. with stirring over 2 hours. After completion of the dropwise addition, the resultant mixture was stirred for 10 hours to bring the reaction to completion. After the reaction mixture was washed four times at 70° C. with water, the toluene and excess epichlorohydrin were distilled out under heat and reduced pressure, whereby a product composed of an amide derivative (4a) as a principal component was obtained (step 5).

To the product obtained above (step 5), composed of the compound (4a) as the principal component and contained in the 10-l five-necked flask, 378.2 g (21.0 mol) of water, 5.83 g (0.070 mol) of a 48% aqueous solution of sodium hydroxide and 32.0 g (0.14 mol) of tetradecanoic acid were added, followed by stirring at 100° C. for 2.5 days under a nitrogen atmosphere. After the reaction mixture was washed three times at 80° C. with a 2% aqueous solution of NaCl, water was eliminated under heat and reduced pressure, whereby 2261.5 g of a product composed of a target compound (1a) as a principal component were obtained (step 6). The product contained the compound (1a) in an amount of 70% and in addition, also contained intermediates, reaction byproducts and the like represented by the following formulae:

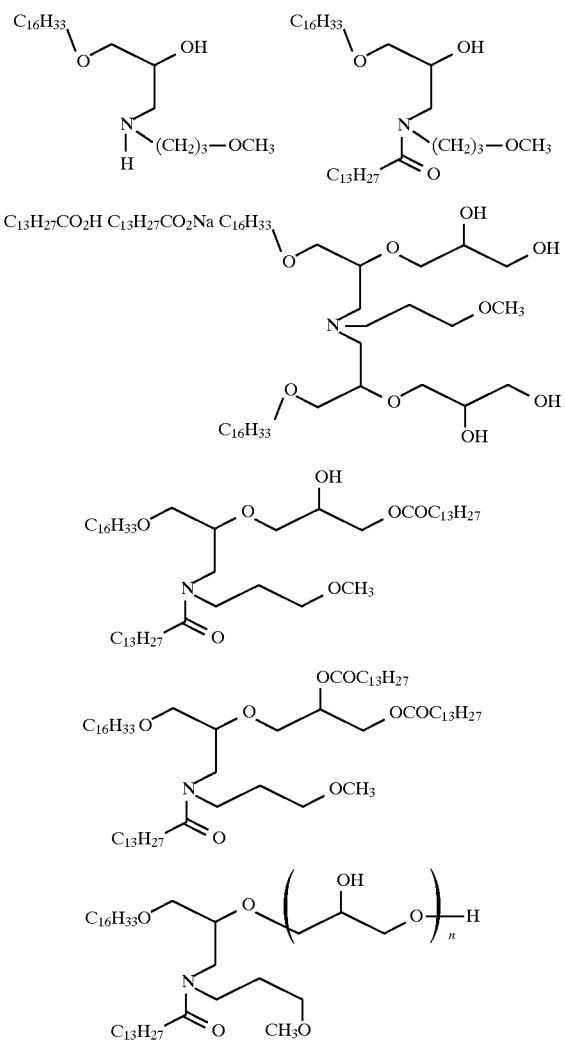

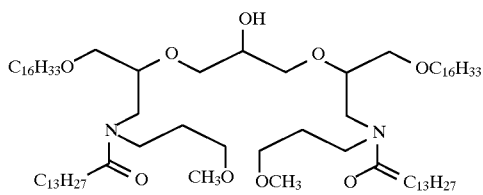
wherein n stands for an integer of 2 to 10.
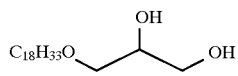
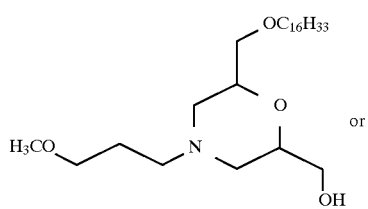
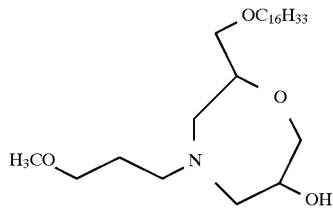
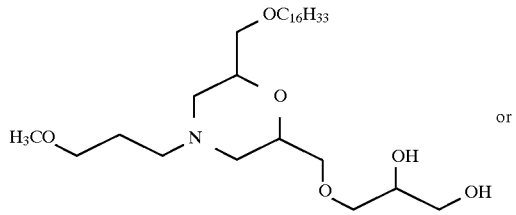 or
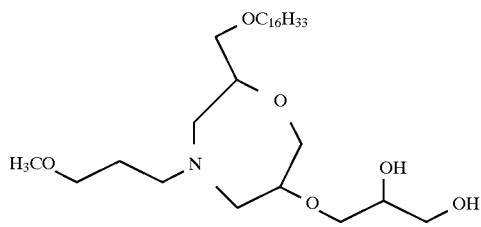
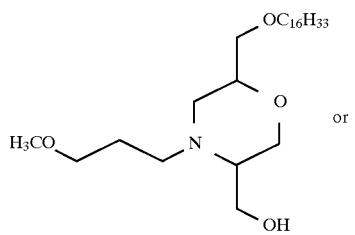 or
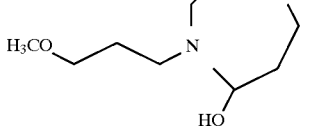
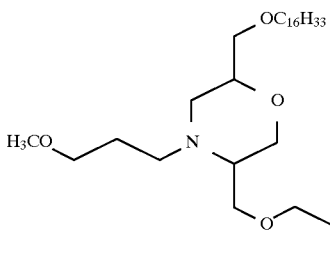
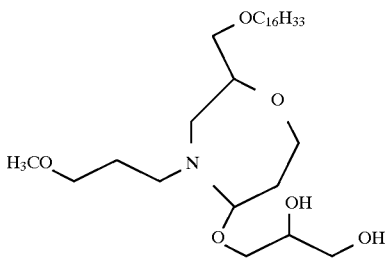 or
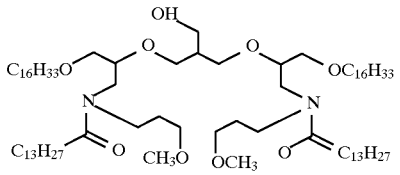
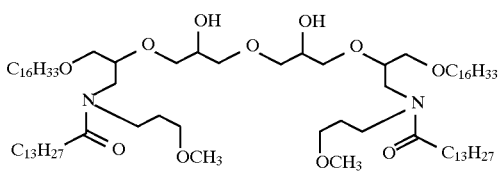
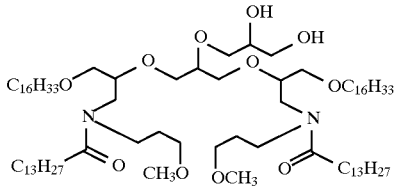
Example 3
An amide derivative (3b) was obtained by conducting reactions as in steps 1 and 2 of Example 1 except that in step 2 of Example 1, methyl hexadecanoate was used in lieu of methyl tetradecanoate (steps 1 and 2).

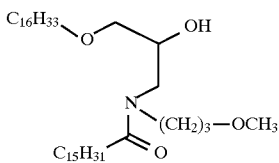

The followings are physical properties of the amide derivative (3b) so obtained.
White solid.
Melting point: 55° C.
IR($\upsilon_{neat}$,cm$^{-1}$): 3430, 2930, 2855, 1620, 1470, 1205, 1110, 950, 720.
$^1$H-NMR(CDCl$_3$,δ): 0.88 (br t,J=6.4 Hz,6 H), 1.26–1.89 (m,57 H), 2.36 (t, J=7.6 Hz,2 H), 3.29–3.52 (m,10 H), 3.33 (s,3 H), 3.88–3.95 (m,1 H).

An amide derivative (4b) was obtained by conducting a reaction as in step 5 of Example 1 except that in step 5 of Example 1, the compound (3b) obtained above (step 2) was used in lieu of the compound (3a) (step 5).

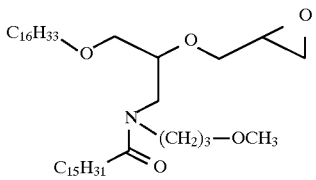

The followings are physical properties of the amide derivative (4b) so obtained.
White solid.
Melting point: 44°–45° C.
IR($\upsilon_{neat}$,cm$^{-1}$): 2930, 2860, 1650, 1470, 1425, 1380, 1210, 1120, 910, 845, 755, 720.
$^1$H-NMR(CDCl$_3$,δ): 0.88 (br t,J=6.7 Hz,6 H), 1.15–1.45 (m,50 H), 1.45–1.73 (m,4 H), 1.73–1.90 (m,2 H), 2.25–2.48 (m,2 H), 2.50–2.68 (m,1 H), 2.70–2.85 (m,1 H), 3.00–3.18 (m,1 H), 3.18–4.00 (m,13 H), 3.32 (s,3 H).

A target amide derivative (1b) was obtained by conducting a reaction as in step 6 of Example 1 except that in step 5 of Example 1 (step 5), the compound (4b) obtained above (step 5) was used in lieu of the compound (4a) and hexadecanoic acid was employed in place of tetradecanoic acid (step 6).

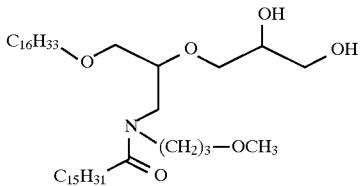

The followings are physical properties of the amide derivative (1b) so obtained.
White solid.
Melting point: 33° C.
IR($\upsilon_{neat}$,cm$^{-1}$): 3445, 2930, 2860, 1650, 1630, 1470, 1420, 1380, 1305, 1210, 1120, 1080.
$^1$H-NMR(CDCl$_3$,δ): 0.88 (br t,J=6.4 Hz,6 H), 1.15–1.45 (m,50 H), 1.45–1.95 (m,7 H), 2.25–2.55 (m,3 H), 3.20–3.92 (m,16 H), 3.33 (s,3 H).

Into a 500-ml four-necked flask fitted with a stirrer and a nitrogen inlet tube, 34.1 g (50.0 mmol) of the compound (4b) obtained above (step 5), 25.5 g (250.0 mmol) of acetic anhydride and 25.3 g (250.0 mmol) of triethylamine were charged, followed by stirring at 100° C. for 10 hours under a nitrogen atmosphere. The reaction mixture was concentrated under heat and reduced pressure and the residue so obtained was purified by chromatography on a silica gel column, whereby 34.9 g of an ester-amide derivative (14b) were obtained (yield: 89%) (step 7).

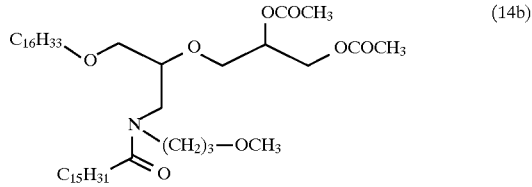

The followings are physical properties of the ester-amide derivative (14b) so obtained.
Brown clear liquid.
$^1$H-NMR(CDCl$_3$,δ): 0.88 (br t,J=6.4 Hz,6 H), 1.26–1.83 (m,56 H), 2.03–2.20 (m,6 H), 2.33 (t, J=7.1 Hz,2 H), 3.12–4.35 (m,15 H), 3.32 (s,3 H), 5.04–5.43 (m,1 H).

Into a 200-ml four-necked flask fitted with a stirrer and a nitrogen inlet tube, 33.9 g (43.2 mmol) of the compound (14b) obtained above (step 7), 0.42 g (2.16 mmol) of a 28% methanol solution of sodium methoxide and 200 ml of methanol were charged, followed by stirring at room temperature for 3.5 hours under a nitrogen atmosphere. The reaction mixture was concentrated under heat and reduced pressure and the residue so obtained was purified by chromatography on a silica gel column, whereby 16.0 g of a target amide derivative (1b) were obtained (yield 53%) (step 8).

Into a 3-l four-necked flask fitted with a stirrer and a nitrogen inlet tube, 45.2 g (72.0 mmol) of the compound (3b) obtained above (step 2), 2.86 g (119.2 mmol) of sodium hydride and 800 ml of toluene were charged, followed by stirring at 55° C. for 30 minutes under a nitrogen atmosphere. Next, 34.8 g (121.5 mmol) of 1,2-isopropylidenedioxy-3-tosyloxypropane were added to the resultant mixture, followed by stirring at 100° C. for 18 hours. The reaction mixture was added under ice cooling with 20 ml of 2-propanol to inactivate unreacted sodium hydride and was then concentrated under heat and reduced pressure. The residue so obtained was purified by chromatography on a silica gel column, whereby 51.0 g of a 1,3-dioxolaneamide derivative (16b) were obtained (yield: 96%) (step 11).

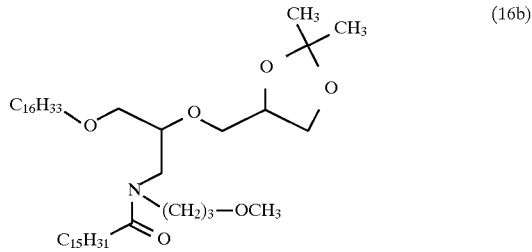

The followings are physical properties of the 1,3-dioxolane-amide derivative (16b) so obtained.
Colorless clear liquid.
$^1$H-NMR(CDCl$_3$,δ): 0.88 (br t,J=6.4 Hz,6 H), 1.20–1.90 (m,62 H), 2.36 (t,J=7.0 Hz,2 H), 3.30–4.25 (m,19 H).

Into a 2-l four-necked flask fitted with a stirrer and a nitrogen inlet tube, 51.0 g (68.9 mmol) of the compound (16b) obtained above (step 11), 0.50 g (2.63 mmol) of tosyl acid monohydrate and 500 ml of methanol, followed by stirring at room temperature for 12 hours under a nitrogen atmosphere. The reaction mixture was concentrated under heat and reduced pressure and the residue so obtained was purified by chromatography on a silica gel column, whereby 41.0 g of a target amide derivative (1b) were obtained (yield: 85%) (step 10).

Example 4

An amide derivative (3c) was obtained by conducting reactions as in step 1 and step 2 of Example 1 except that in step 2 of Example 1, methyl dodecanoate was used instead of methyl tetradecanoate (steps 1 and 2).

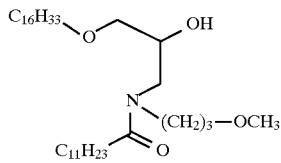
(3c)

The followings are physical properties of the amide derivative (3c) so obtained.
Colorless clear liquid.
IR($\upsilon_{neat}$,cm$^{-1}$): 3435, 2930, 2855, 1620, 1470, 1220, 1110, 720.
$^1$H-NMR(CDCl$_3$,δ): 0.88 (br t,J=6.4 Hz,6 H), 1.20–1.90 (m,49 H), 2.36(t,J=7.6 Hz,2 H), 3.25–3.52 (m,10 H), 3.33 (s,3H), 3.88–3.95 (m,1 H).

An amide derivative (4c) was obtained by conducting a reaction as in step 5 of Example 1 except that in step 5 of Example 1, the compound (3c) obtained above (step 2) was used in lieu of the compound (3a) (step 5).

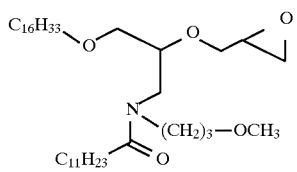
(4c)

The followings are physical properties of the amide derivative (4c) so obtained.
Pale yellow liquid.
IR($\upsilon_{neat}$,cm$^{-1}$): 2940, 2875, 1750, 1650, 1470, 1380, 1210, 1120, 910, 845.
$^1$H-NMR(CDCl$_3$,δ): 0.88 (br t,J=6.4 Hz,6 H), 1.15–1.45 (m,42 H), 1.45–1.75 (m,4 H), 1.75–1.90 (m,2 H), 2.25–2.50 (m,2 H), 2.50–2.68 (m,1 H), 2.70–2.85 (m,1 H), 3.00–3.18 (m,1 H), 3.18–4.00 (m,13 H), 3.32 (s,3 H).

A target amide derivative (1c) was obtained by conducting reactions as in step 7 and step 8 of Example 1 except that in step 7 of Example 1, the compound (4c) obtained above (step 5) was used instead of the compound (4a) (steps 7 and 8).

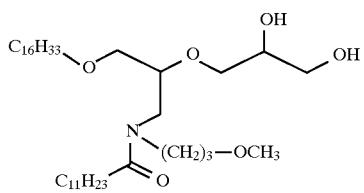
(1c)

The followings are physical properties of the amide derivative (1c) so obtained.
Colorless clear liquid.
IR($\upsilon_{neat}$,cm$^{-1}$): 3430, 2930, 2860, 1650, 1630, 1470, 1380, 1260, 1210, 1115, 1080, 795, 720.
$^1$H-NMR(CDCl$_3$,δ): 0.88 (br t,J=6.7 Hz,6 H), 1.15–1.45 (m,42 H), 1.45–1.97 (m,8 H), 2.25–2.45 (m,2 H), 3.15–3.92 (m,16 H), 3.33 (s,3 H).

Example 5

An amide derivative (3d) was obtained by conducting reactions as in step 1 and step 2 of Example 1 except that in step 2 of Example 1, the methyl ester of "Lunac P-70" (trade name for a 3:70:27 mixture by weight ratio of tetradecanoic acid, hexadecanoic acid and octadecanoic acid; product of Kao Corporation), said methyl ester having been prepared by reacting "Lunac P-70" with methanol in the presence of sulfuric acid as a catalyst under heat and reflux, was used in place of methyl decanoate (steps 1 and 2).

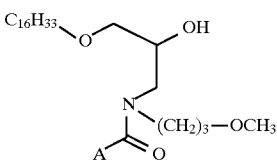
(3d)

wherein A represents a mixture of $C_{13}H_{27}$—, $C_{15}H_{31}$— and $C_{17}H_{35}$—.

The followings are physical properties of the amide derivative (3d) so obtained.
White solid.
Melting point: 50° C.
IR($\upsilon_{neat}$,cm$^{-1}$): 3430, 2930, 2860, 1620, 1470, 1205, 1110, 950, 720.

A target amide derivative (1d) was obtained by conducting reactions as in step 11 and step 10 of Example 3 except that in step 11 of Example 3, the reaction was conducted using the compound (3d), which had been obtained above (step 2), instead of the compound (3b) and in the next step 10, the reaction was conducted without purification of the thus-obtained 1,3-dioxolane-amide derivative (16d) (steps 11 and 10).

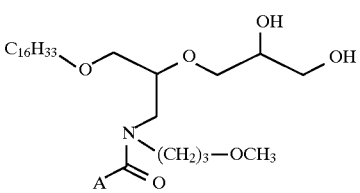
(1d)

wherein A represents a mixture of $C_{13}H_{27}$—, $C_{15}H_{31}$— and $C_{17}H_{35}$—.

The followings are physical properties of the amide derivative (1d) so obtained.
White solid.
Melting point: 32° C.
IR($\upsilon_{neat}$,cm$^{-1}$): 3445, 2930, 2860, 1650, 1630, 1470, 1380, 1210, 1120, 1080, 720.

Example 6

An aminoalcohol derivative (2e) was obtained by conducting a reaction as in step 1 of Example 1 except that in step 1 of Example 1, octadecyl glycidyl ether was used instead of hexadecyl glycidyl ether (step 1).

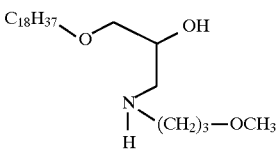
(2e)

The followings are physical properties of the amino alcohol derivative (2e) so obtained.
White solid.

Melting point: 57°–58° C.
IR($\upsilon_{neat}$,cm$^{-1}$): 3340, 2930, 2855, 1470, 1120, 960, 900, 840.
$^1$H-NMR(CDCl$_3$,δ): 0.88 (t,J=6.3 Hz,3 H), 1.25–1.45 (m,30 H), 1.45–1.85 (m,6 H), 2.55–2.75 (m,4 H), 3.32 (s,3 H), 3.35–3.50 (m,6 H), 3.77–3.89 (m,1 H).

An amide derivative (3e) was obtained by conducting a reaction as in step 2 of Example 1 except that in step 2 of Example 1, the compound (2e) obtained above (step 1) was used in lieu of the compound (2a) (step 2).

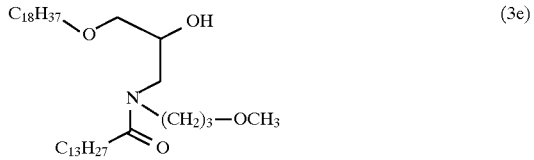

The followings are physical properties of the amide derivative (3e) so obtained.
White solid.
Melting point: 49° C.
IR($\upsilon_{neat}$,cm$^{-1}$): 3440, 2930, 2860, 1650, 1625, 1470, 1225, 1210, 1110, 950, 720.
$^1$H-NMR(CDCl$_3$,δ): 0.88 (br t,J=6.3 Hz,6 H), 1.15–1.95 (m,57 H), 2.36 (t,J=7.5 Hz,2 H), 3.30–3.55 (m,10 H), 3.33 (s,3 H), 3.85–3.95 (m,1 H).

An amide derivative (4e) was obtained by conducting a reaction as in step 5 of Example 1 except that in step 5 of Example 1, the compound (3e) obtained above (step 2) was used instead of the compound (3a) (step 5).

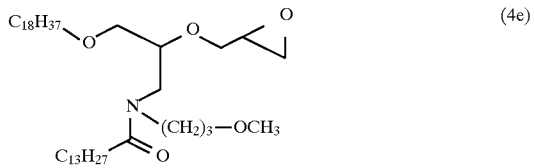

The followings are physical properties of the amide derivative (4e) so obtained.
Colorless clear liquid.
IR($\upsilon_{neat}$,cm$^{-1}$): 2930, 2860, 1650, 1425, 1380, 1260, 1210, 1120, 910, 720.
$^1$H-NMR(CDCl$_3$,δ): 0.88 (br t,J=6.0 Hz,6 H), 1.10–1.45 (m,50 H), 1.45–1.90 (m,6 H), 2.25–2.50 (m,2 H), 2.50–2.68 (m,1 H), 2.70–2.85 (m,1 H), 3.01–3.20 (m,1 H), 3.20–4.00 (m,13 H), 3.32 (s,3 H).

A target amide derivative (1e) was obtained by conducting reactions as in steps 7 and 8 of Example 1 except that in step 7 of Example 1, the compound (4e) obtained above (step 5) was used instead of the compound (4a) (steps 7 and 8).

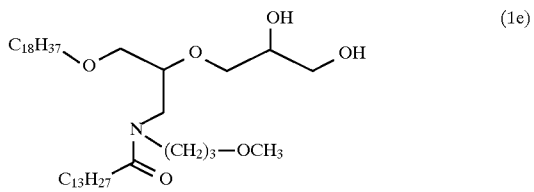

The followings are physical properties of the amide derivative (1e) so obtained.
White solid.
Melting point: 23° C.
IR($\upsilon_{neat}$,cm$^{-1}$): 3425, 2930, 2860, 1650, 1630, 1470, 1380, 1220, 1210, 1120, 720.
$^1$H-NMR(CDCl$_3$,δ): 0.88 (br t,J=6.7 Hz,6 H), 1.17–1.45 (m,49 H), 1.45–1.92 (m,8 H), 2.22–2.45 (m,2 H), 3.20–3.90 (m,17 H), 3.33 (s,3 H).

Example 7

An amide derivative (3f) was obtained by conducting a reaction as in step 2 of Example 1 except that in step 2 of Example 1, the compound (2e) obtained in step 1 of Example 6 was used instead of the compound (2a) and methyl hexadecanoate was employed in place of methyl tetradecanoate (steps 1 and 2).

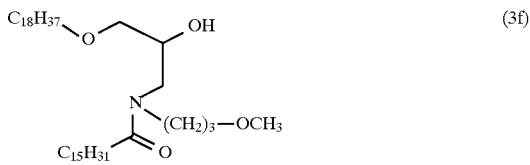

The followings are physical properties of the amide derivative (3f) so obtained.
White solid.
Melting point: 54°–55° C.
IR($\upsilon_{neat}$,cm$^{-1}$): 3430, 2930, 2855, 1620, 1470, 1220, 1205, 1110, 950, 885, 720.
$^1$H-NMR(CDCl$_3$,δ): 0.88 (br t,J=6.4 Hz,6 H), 1.25–1.95 (m,61 H), 2.36 (t,J=7.6 Hz,2 H), 3.29–3.52 (m,10 H), 3.33 (s,3 H), 3.88–3.95 (m,1 H).

An amide derivative (4f) was obtained by conducting a reaction as in step 5 of Example 1 except that in step 5 of Example 1, the compound (3f) was used instead of the compound (3a) (step 5).

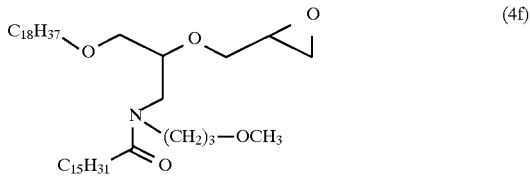

The followings are physical properties of the amide derivative (4f) so obtained.
White solid.
Melting point: 45°–47° C.
IR($\upsilon_{neat}$,cm$^{-1}$): 2930, 2860, 1650, 1470, 1425, 1380, 1210, 1120, 910, 845, 755, 720.
$^1$H-NMR(CDCl$_3$,δ): 0.88 (br t,J=6.7 Hz,6 H), 1.15–1.45 (m,54 H), 1.45–1.73 (m,4 H), 1.73–1.90 (m,2 H), 2.25–2.48 (m,2 H), 2.50–2.68 (m,1 H), 2.70–2.85 (m,1 H), 3.00–3.18 (m,1 H), 3.18–4.00 (m,13 H), 3.32 (s,3 H).

A target amide derivative (1f) was obtained by conducting reactions as in steps 7 and 8 of Example 1 except that in step 7 of Example 1, the compound (4f) obtained above (step 5) was used instead of the compound (4a) (steps 7 and 8).

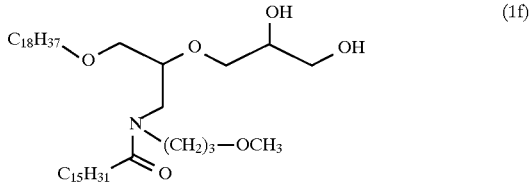

The followings are physical properties of the amide derivative (1f) so obtained.
White solid.
Melting point: 35° C.
IR($\upsilon_{neat}$,cm$^{-1}$): 3445, 2930, 2860, 1630, 1470, 1420, 1380, 1305, 1210, 1120, 1080.
$^1$H-NMR(CDCl$_3$,δ): 0.88 (br t,J=6.4 Hz,6 H), 1.15–1.45 (m,54 H), 1.45–1.95 (m,7 H), 2.25–2.55 (m,3 H), 3.20–3.95 (m,16 H), 3.33 (s,3 H).

Example 8

An amino alcohol (2g) was obtained by conducting a reaction as in step 1 of Example 1 except that in step 1 of Example 1, tetradecyl glycidyl ether was employed in lieu of hexadecyl glycidyl ether (step 1).

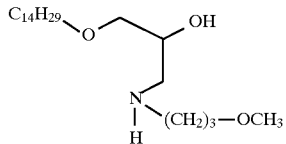

The followings are physical properties of the amino alcohol derivative (2g) so obtained.
White solid.
Melting point: 47° C.
IR($\upsilon_{neat}$,cm$^{-1}$): 3340, 2930, 2855, 1470, 1310, 1120, 1065, 995, 900, 720.
$^1$H-NMR(CDCl$_3$,δ): 0.88 (t,J=6.3 Hz,3 H), 1.25–1.45 (m,26 H), 1.45–1.85 (m,6 H), 2.57–2.75 (m,4 H), 3.32 (s,3 H), 3.38–3.48 (m,6 H), 3.75–3.88 (m,1 H).

An amide derivative (3g) was obtained by conducting a reaction as in step 2 of Example 1 except that in step 2 of Example 1, the compound (2g) obtained above (step 1) was used instead of the compound (2a) and methyl hexadecanoate was used in place of methyl tetradecanoate (step 2).

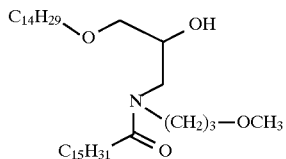

The followings are physical properties of the amide derivative (3g) so obtained.
White solid.
Melting point: 47° C.
IR($\upsilon_{neat}$,cm$^{-1}$): 3440, 2430, 2855, 1620, 1470, 1205, 1110, 950, 720.
$^1$H-NMR(CDCl$_3$,δ): 0.88 (br t,J=6.4 Hz,6 H), 1.26–1.89 (m,52 H), 2.36 (t,J=7.6 Hz,2 H), 3.29–3.52 (m,11 H), 3.33 (s,3 H), 3.88–3.95 (m,1 H).

An amide derivative (4g) was obtained by conducting a reaction as in step 5 of Example 1 except that in step 5 of Example 1, the compound (3g) obtained above (step 2) was used instead of the compound (3a) (step 5).

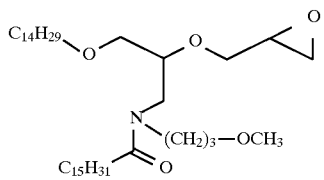

The followings are physical properties of the amide derivative (4g) so obtained.
Colorless clear liquid.
IR($\upsilon_{neat}$,cm$^{-1}$): 2930, 2860, 1650, 1470, 1425, 1380, 1210, 1120, 910, 845, 755, 720.
$^1$H-NMR(CDCl$_3$,δ): 0.88 (br t,J=6.7 Hz,6 H), 1.15–1.45 (m,46 H), 1.45–1.73 (m,4 H) 1.73–1.90 (m,2 H), 2.25–2.50 (m,2 H), 2.50–2.68 (m,1 H), 2.70–2.85 (m,1 H), 3.00–3.18 (m,1 H), 3.18–4.00 (m,13 H), 3.32 (s,3 H).

A target amide derivative (1g) was obtained by conducting reactions as in steps 7 and 8 of Example 1 except that in step 7 of Example 1, the compound (4g) obtained above (step 5) was used instead of the compound (4a) (steps 7 and 8).

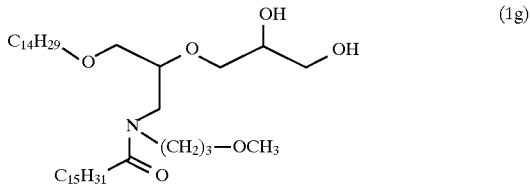

The followings are physical properties of the amide derivative (1g) so obtained.
White solid.
Melting point: 27° C.
IR($\upsilon_{neat}$,cm$^{-1}$): 3445, 2930, 2860, 1650, 1630, 1470, 1420, 1380, 1305, 1210, 1120, 1080, 720.
$^1$H-NMR(CDCl$_3$,δ): 0.88 (br t,J=6.4 Hz,6 H), 1.15–1.45 (m,45 H), 1.45–1.93 (m,7 H), 2.20–2.60 (m,3 H), 3.20–3.90 (m,17 H), 3.33 (s,3 H).

Example 9

An amino alcohol derivative (2h) was obtained by conducting a reaction as in step 1 of Example 1 except that in step 1 of Example 1, 2-methoxyethylamine was used instead of 3-methoxypropylamine (step 1).

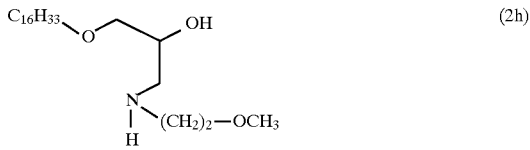

The followings are physical properties of the amino alcohol derivative (2h) so obtained.
White solid.
Melting point: 54°–55° C.
IR($\upsilon_{neat}$,cm$^{-1}$): 3430, 2920, 2855, 1470, 1120, 1065, 900, 720.
$^1$H-NMR(CDCl$_3$,δ): 0.88 (br t,J=6.3 Hz,3 H), 1.25–1.70 (m,30 H), 2.57–2.76 (m,4 H), 3.32 (s,3 H), 3.38–3.48 (m,6 H), 3.77–3.89 (m,1 H).

An amide derivative (3h) was obtained by conducting a reaction as in step 2 of Example 1 except that in step 2 of Example 1, the compound (2h) obtained above (step 1) was used instead of the compound (2a) and methyl hexadecanoate was used in place of methyl tetradecanoate (step 2).

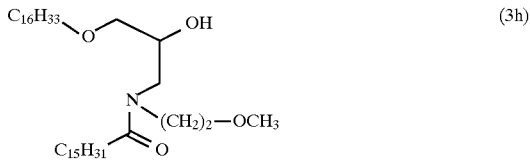

The followings are physical properties of the amide derivative (3h) so obtained.
White solid.
Melting point: 51°–52° C.
IR($\upsilon_{neat}$,cm$^{-1}$): 3420, 2920, 2855, 1620, 1470, 1110, 720.
$^1$H-NMR(CDCl$_3$,δ): 0.87 (br t,J=6.4 Hz,6 H), 1.15–1.70 (m,55 H), 2.25–2.50 (m,2 H), 3.20–4.00 (m,11 H), 3.34 (s,3 H).

An amide derivative (4h) was obtained by conducting a reaction as in step 5 of Example 1 except that in step 5 of Example 1, the compound (3h) obtained above (step 2) was used instead of the compound (3a) (step 5).

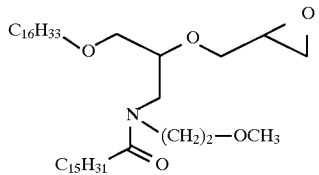

The followings are physical properties of the amide derivative (4h) so obtained.
Colorless clear liquid.
IR($v_{neat}$,cm$^{-1}$): 2930, 2855, 1650, 1470, 1420, 1380, 1310, 1250, 1190, 1120, 910, 850, 720.
$^1$H-NMR(CDCl$_3$,δ): 0.88 (br t,J=6.4 Hz,6 H), 1.13–1.45 (m,50 H), 1.45–1.70 (m,4 H), 2.30–2.50 (m,2 H), 2.50–2.70 (m,1 H), 2.70–2.85 (m,1 H), 3.00–3.20 (m,1 H), 3.20–4.00 (m,13 H), 3.32 (s,3 H).

A target amide derivative (1 h) was obtained by conducting a reaction as in step 6 of Example 1 except that in step 6 of Example 1, the compound (4h) obtained above (step 5) was used instead of the compound (4a) (step 6).

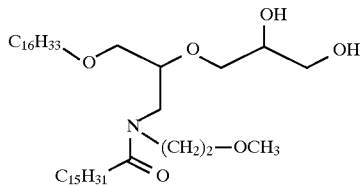

The followings are physical properties of the amide derivative (1h) so obtained.
White solid.
Melting point: 31°–32° C.
IR($v_{neat}$,cm$^{-1}$): 3450, 2930, 2860, 1630, 1470, 1380, 1300, 1190, 1160, 720.
$^1$H-NMR(CDCl$_3$,δ): 0.88 (t,J=6.4 Hz,6 H), 1.15–1.75 (m,54 H), 2.20–2.45 (m,3 H), 3.20–3.90 (m,17 H), 3.33 (s,3 H).

A 1,3-dioxolane-amide derivative (16h) was obtained by conducting a reaction as in step 11 of Example 3 except that in step 11 of Example 3, the compound (3h) obtained above (step 2) was used instead of the compound (3b) (step 11).

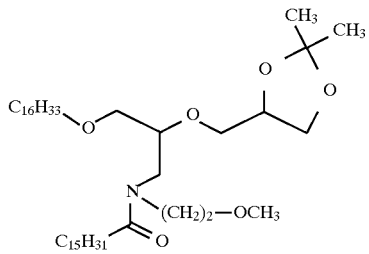

The followings are physical properties of the 1,3-dioxolane-amide derivative (16h) so obtained.
Colorless clear liquid.
$^1$H-NMR(CDCl$_3$,δ): 0.88 (br t,J=6.4 Hz,6 H), 1.15–1.70 (m,54 H), 1.34 (s,3 H), 1.40 (s,3 H), 2.36 (t,J=7.0 Hz,2 H), 3.25–4.30 (m,19 H).

A target amide derivative (1h) was obtained by conducting a reaction as in step 11 of Example 3 except that in step 10 of Example 3, the compound (16h) obtained above (step 11) was used instead of the compound (16b) (step 10).

Example 10

An amino alcohol derivative (2i) was obtained by conducting a reaction as in step 1 of Example 1 except that in step 1 of Example 1, ethylamine was used instead of 3-methoxypropylamine (step 1).

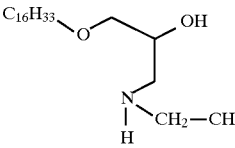

The followings are physical properties of the amino alcohol derivative (2i) so obtained.
White solid.
Melting point: 60°–61° C.
IR($v_{neat}$,cm$^{-1}$): 3400, 2930, 2855, 1470, 1310, 1110, 955, 720.
$^1$H-NMR(CDCl$_3$,δ): 0.88 (t,J=6.4 Hz,3 H), 1.11 (t,J=7.2 Hz,3 H), 1.15–1.70 (m,30 H), 2.55–2.80 (m,4 H), 3.35–3.53 (m,4 H), 3.79–3.93 (m,1 H).

An amide derivative (3i) was obtained by conducting a reaction as in step 2 of Example 1 except that in step 2 of Example 1, the compound (2i) obtained above (step 1) was used instead of the compound (2a) and methyl hexadecanoate was used in place of methyl tetradecanoate (step 2).

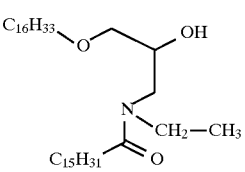

The followings are physical properties of the amide derivative (3i) so obtained.
White solid.
Melting point: 56° C.
IR($v_{neat}$,cm$^{-1}$): 3410, 2930, 2860, 1625, 1470, 1380, 1305, 1245, 1210, 1110, 950, 855, 720.
$^1$H-NMR(CDCl$_3$,δ): 0.88 (t,J=6.4 Hz,6 H), 1.15–1.75 (m,57 H), 2.34 (t,J=7.6 Hz,2 H), 3.30–3.55 (m,9 H), 3.85–4.00 (m,1H).

An amide derivative (4i) was obtained by conducting a reaction as in step 5 of Example 1 except that in step 5 of Example 1, the compound (3i) obtained above (step 2) was used instead of the compound (3a) (step 5).

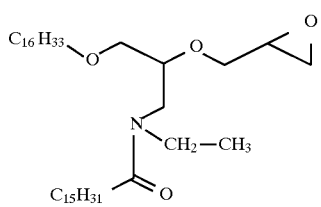

The followings are physical properties of the amide derivative (4i) so obtained.
Colorless clear liquid.
IR($v_{neat}$,cm$^{-1}$): 2930, 2855, 1650, 1470, 1425, 1380, 1210, 1120, 905, 840, 720.
$^1$H-NMR(CDCl$_3$,δ): 0.88 (br t,J=6.4 Hz,6 H), 1.10–1.75 (m,57 H), 2.25–2.50 (m,2 H), 2.50–2.70 (m,1 H), 2.70–2.85 (m,1 H), 3.00–4.00 (m,12 H).

A target amide derivative (1i) was obtained by conducting a reaction as in step 6 of Example 1 except that in step 6 of Example 1, the compound (4i) obtained above (step 5) was used instead of the compound (4a) (step 6).

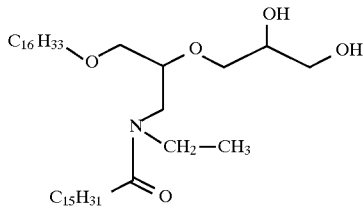

(1i)

The followings are physical properties of the amide derivative (1i) so obtained.
White solid.
Melting point: 35°–36° C.
IR($\upsilon_{neat}$,cm$^{-1}$): 3445, 2930, 2860, 1630, 1470, 1420, 1380, 1305, 1210, 1120, 720.
$^1$H-NMR(CDCl$_3$,δ): 0.88 (br t,J=6.4 Hz,6 H), 1.13–1.75 (m,57 H), 2.31 (t,J=7.5 Hz, 2 H), 3.20–3.90 (m,16 H).

Example 11

An amino alcohol derivative (2j) was obtained by conducting a reaction as in step 1 of Example 1 except that in step 1 of Example 1, ethanolamine was used instead of 3-methoxypropylamine (step 1).

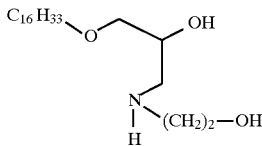

(2j)

The followings are physical properties of the amino alcohol derivative (2j) so obtained.
White solid.
Melting point: 70°–73° C.
$^1$H-NMR(CDCl$_3$,δ): 0.85 (t,J=6.4 Hz,3 H), 1.23 (br s, 28 H), 2.60–2.80 (m,4 H), 3.10–3.90 (m,10 H).

An amide derivative (3j) was obtained by conducting a reaction as in step 2 of Example 1 except that in step 2 of Example 1, the compound (2j) obtained above (step 1) was used instead of the compound (2a) and methyl hexadecanoate was used in place of methyl tetradecanoate (step 2).

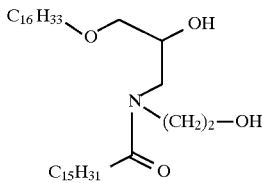

(3j)

The followings are physical properties of the amide derivative (3j) so obtained.
White solid.
Melting point: 75° C.
IR($\upsilon_{neat}$,cm$^{-1}$): 3320, 2925, 2850, 1615, 1470, 1440, 1380, 1110, 1060, 720.
$^1$H-NMR(CDCl$_3$,δ): 0.86 (t,J=6.4 Hz,6 H), 1.00–1.60 (m,54 H), 2.20–2.50 (m,2 H), 3.10–4.10 (m,13 H).

Into a 500-ml four-necked flask fitted with a stirrer, a dropping funnel and a nitrogen inlet tube, 15.2 g (0.042 mol) of the compound (2j) obtained above (step 1), 10.0 g (0.126 mol) of pyridine and 200 ml of chloroform were charged. While the contents were stirred under ice cooling and a nitrogen atmosphere, 34.6 g (0.126 mol) of hexadecanoyl chloride were added dropwise to the resultant mixture over 30 minutes. After completion of the dropwise addition, the reaction mixture was stirred at room temperature for 2 hours. The reaction mixture was washed with water and then concentrated under reduced pressure, whereby 45.1 g of a crude product of an ester-amide derivative (11j) were obtained (step 3).

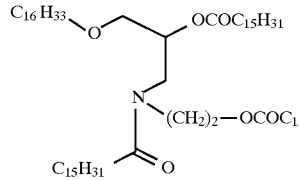

(11j)

The followings are physical properties of the ester-amide derivative (11j) so obtained.
$^1$H-NMR(CDCl$_3$,δ): 0.86 (br t,J=6.4 Hz,12 H), 1.25 (br s, 106 H), 2.20–2.40 (m,6 H), 3.30–3.60 (m,8 H), 4.00–4.30 (m,2 H), 5.10–5.20 (m,1 H).

Into a 1-l four-necked flask fitted with a stirrer, 45.1 g of the compound (11j) obtained above (step 3), 5.8 g (0.084 mol) of potassium carbonate and 450 g of a 1:1 mixed solvent of water and methanol were charged, followed by stirring under heat and reflux for 3 hours. A chloroform-soluble substance was extracted from the reaction mixture and purified by chromatography on a silica gel column, whereby 15.0 g of an amide derivative (3j) were obtained [yield: 60% based on the compound (2j)] (step 4).

Into a 200-ml four-necked flask fitted with a stirrer and a nitrogen inlet tube, 10.0 g (16.7 mmol) of the compound (3j) obtained above (step 2), 0.162 g (0.50 mmol) of tetrabutylammonium bromide, 6.49 g (70.1 mmol) of epichlorohydrin, 2.77 g (69.3 mmol) of sodium hydroxide and 20 g of a 1:1 mixed solvent of toluene and dioxane were charged, followed by stirring at 40° C. for 15 hours under a nitrogen atmosphere. After the resulting reaction mixture was diluted with toluene, the toluene solution so obtained was washed with water and then with a saturated aqueous solution of NaCl, followed by concentration under heat and reduced pressure. The thus-obtained residue was purified by chromatography on a silica gel column, whereby 6.9 g of an amide derivative (4j) were obtained (yield: 58%) (step 5).

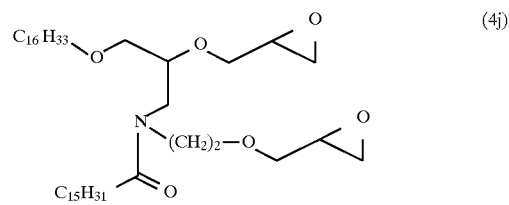

(4j)

The followings are physical properties of the amide derivative (4j) so obtained.
White solid.
Melting point: 42°–43° C.
IR($\upsilon_{neat}$,cm$^{-1}$): 2930, 2855, 1650, 1470, 1420, 1380, 1250, 1210, 1115, 910, 845, 755, 720.
$^1$H-NMR(CDCl$_3$,δ): 0.88 (br t,J=6.3 Hz,6 H), 1.10–1.42 (m,50 H), 1.45–1.70 (m,4 H), 2.30–2.50 (m,2 H), 2.50–2.68 (m,2 H), 2.70–2.85 (m,2 H), 3.00–3.20 (m,2 H), 3.20–4.00 (m,15 H).

A target amide derivative (1i) was obtained by conducting a reaction as in step 6 of Example 1 except that in step 6 of Example 1, the compound (4j) obtained above (step 5) was used instead of the compound (4a) and hexadecanoic acid was used in place of tetradecanoic acid (step 6).

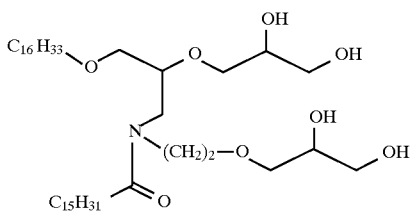

(1j)

The followings are physical properties of the amide derivative (1j) so obtained.
White solid.
Melting point: 60° C.
IR($v_{neat}$,cm$^{-1}$): 3385, 2920, 2855, 1655, 1470, 1420, 1380, 1300, 1205, 1120, 1045, 985, 930, 850, 720.
$^1$H-NMR(CDCl$_3$,δ): 0.88 (br t,J=6.4 Hz,6 H), 1.15–1.45 (m,50 H), 1.45–1.70 (m,4 H), 2.25–2.50 (m,2 H), 3.20–4.10 (m,25 H).

Into a 3-l four-necked flask fitted with a stirrer and a nitrogen inlet tube, 50.3 g (84.1 mmol) of the compound (3j) obtained above (step 2), 8.7 g (362.5 mmol) of sodium hydride and 500 ml of N,N-dimethylformamide were charged, followed by stirring at room temperature for 20 minutes under a nitrogen atmosphere. Next, while the contents were stirred at 60υ under heat and a nitrogen atmosphere, a solution of 73.5 g (256.7 mmol) of 1,2-isopropylidenedioxy-3-tosyloxypropane in 200 ml of N,N-dimethylformamide was added dropwise to the contents over 1 hour. After completion of the dropwise addition, the reaction mixture was stirred further at 80° C. for 8 hours, followed by the addition of water under ice cooling to inactivate unreacted sodium hydride. The mixture so obtained was extracted three times with diethyl ether. The resulting organic layers were combined together, washed twice with a saturated aqueous solution of NaCl, and then concentrated under heat and reduced pressure. The residue so obtained was purified by chromatography on a silica gel column, whereby 40.1 g of a 1,3-dioxolaneamide derivative (16j) were obtained (yield: 58%) (step 11).

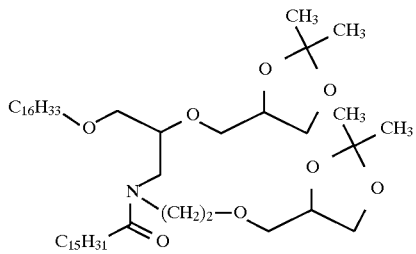

(16j)

The followings are physical properties of the 1,3-dioxolane-amide derivative (16j) so obtained. Colorless clear liquid.
IR($v_{neat}$,cm$^{-1}$): 3000, 2950, 2875, 1660, 1480, 1425, 1380, 1260, 1210, 1120, 1090, 1060, 850, 720.
$^1$H-NMR(CDCl$_3$,δ): 0.88 (br t,J=6.4 Hz,6 H), 1.15–1.48 (m,62 H), 1.34 (s,3 H), 1.36 (s,3 H), 1.40 (s,3 H), 1.41 (s,3 H), 1.48–1.70 (m,4 H), 2.25–2.50 (m,2 H), 3.20–4.40 (m,21 H).

Into a 1-l four-necked flask fitted with a stirrer and a nitrogen inlet tube, 40.1 g (53.2 mmol) of the compound (16j) obtained above (step 11), 1.01 g (5.30 mmol) of tosyl acid monohydrate and 40 ml of a 1:1 mixed solvent of methanol and ethanol were charged, followed by stirring at 40° C. for 20 hours under a nitrogen atmosphere. After 450 mg of sodium bicarbonate were added to the reaction mixture, the resulting mixture was concentrated under heat and reduced pressure. The thus-obtained residue was purified by chromatography on a silica gel column, whereby 30.0 g of a target amide derivative (1j) were obtained (yield: 84%) (step 10).

Example 12

An amide derivative (3k) was obtained by conducting a reaction as in step 2 of Example 1 except that in step 2 of Example 1, the methyl ester of "Lunac P-70" (trade name for a 3:70:27 mixture by weight ratio of tetradecanoic acid, hexadecanoic acid and octadecanoic acid; product of Kao Corporation), said methyl ester having been prepared by reacting "Lunac P-70" with methanol in the presence of sulfuric acid as a catalyst under heat and reflux, was used in place of methyl decanoate (steps 1 and 2).

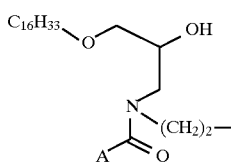

(3k)

wherein A represents a mixture of $C_{13}H_{27}$—, $C_{15}H_{31}$— and $C_{17}H_{35}$—.

The followings are physical properties of the amide derivative (3k) so obtained.
White solid.
Melting point: 72°–75° C.
IR($v_{neat}$,cm$^{-1}$): 3320, 2925, 2850, 1615, 1470, 1440, 1380, 1110, 1060, 720.

A target amide derivative (1k) was obtained by conducting reactions as in step 11 and step 10 of Example 11 except that in step 11 of Example 11, the reaction was conducted using the compound (3k), which had been obtained above (step 2), instead of the compound (3j) and in the next step 10, the reaction was conducted without purification of the thus-obtained 1,3-dioxolane-amide derivative (16k) (steps 11 and 10).

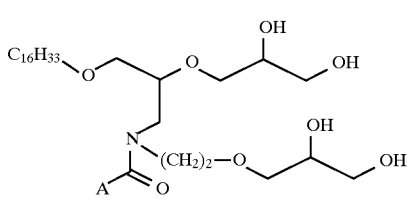

(1k)

wherein A represents a mixture of $C_{13}H_{27}$—, $C_{15}H_{31}$— and $C_{17}H_{35}$—.

The followings are physical properties of the amide derivative (1k) so obtained.
White solid.
Melting point: 42°–43° C.
IR($v_{neat}$,cm$^{-1}$): 3390, 2920, 2855, 1655, 1470, 1420, 1380, 1300, 1205, 1120, 1045, 985, 930, 850, 720.

Example 13

The amide derivatives, which had been prepared in Examples 1 to 12, respectively, were each mixed with vaseline at an amide derivative/vaseline ratio of 1/3 (by weight). With respect to each of the resultant mixtures, a skin conductance and skin roughness were evaluated by the below-described methods, respectively. The results are presented in Table 1.
(Testing methods)
Ten female volunteers of ages ranging from 20 to 50 with skin roughness at their cheeks in winter were chosen as subjects. Different external skin care preparations were coated on the left and right cheeks of each subject for 2 weeks. On the following day after the completion of the coating for 2 weeks, tests were conducted with respect to the following items:

(1) Skin conductance

After washing the face with warm water of 37° C., each subject quietly stayed for 20 minutes in a room controlled at a temperature of 20° C. and a humidity of 40%. The water content of her skin horny layer was measured by a skin conductance meter (manufactured by IBS Corp.). The smaller the conductance value, the rougher the skin. A conductance value of 5 or lower indicates severe skin roughness. On the other hand, no skin roughness is practically recognizable when this value is 20 or greater.

(2) Score of skin roughness

Skin roughness was visually observed and ranked in accordance with the below-described standards. The score was indicated by an average value.

0: No skin roughness is observed.
1: Slight skin roughness is observed.
2: Skin roughness is observed.
3: Rather severe skin roughness is observed.
4: Severe skin roughness is observed.

TABLE 1

| | Skin conductance | Score of skin roughness |
|---|---|---|
| Amide derivative (1a) of Ex. 1 | 28 | 0.6 |
| Amide derivative (1a) of Ex. 2 | 26 | 0.7 |
| Amide derivative (1b) of Ex. 3 | 23 | 0.9 |
| Amide derivative (1c) of Ex. 4 | 25 | 0.8 |
| Amide derivative (1d) of Ex. 5 | 19 | 1.0 |
| Amide derivative (1e) of Ex. 6 | 17 | 1.2 |
| Amide derivative (1f) of Ex. 7 | 19 | 1.1 |
| Amide derivative (1g) of Ex. 8 | 18 | 1.2 |
| Amide derivative (1h) of Ex. 9 | 21 | 1.0 |
| Amide derivative (1i) of Ex. 10 | 13 | 1.6 |
| Amide derivative (1j) of Ex. 11 | 17 | 1.3 |
| Amide derivative (1k) of Ex. 12 | 17 | 1.3 |
| Comparative product (vaseline alone) | 6 | 2.4 |

Example 14

Using certain amide derivatives according to the present invention, external skin care preparations (emulsified cosmetics) of the compositions shown below in Table 2 were formulated. Their skin-roughness-lessening effects were evaluated in the same manner as in Example 13. The results are presented in Table 3.

TABLE 2

| | Invention product | Comparative product |
|---|---|---|
| Methyl-branched isostearyl glyceryl ether | 2.0 | 2.0 |
| 2-Octyldodecyl myristate | 10.0 | 10.0 |
| Vaseline | 3.0 | 3.0 |
| Squalane | 5.0 | 5.0 |
| Tocopherol acetate | 0.5 | 0.5 |
| Invention amide derivative | 1.0 | — |
| Water | Balance | Balance |

TABLE 3

| | Score of skin roughness |
|---|---|
| Amide derivative (1a) of Ex. 1 | 0.6 |
| Amide derivative (1a) of Ex. 2 | 0.6 |
| Amide derivative (1b) of Ex. 3 | 0.9 |
| Amide derivative (1c) of Ex. 4 | 0.8 |
| Amide derivative (1d) of Ex. 5 | 1.0 |
| Amide derivative (1e) of Ex. 6 | 1.0 |
| Amide derivative (1f) of Ex. 7 | 0.9 |
| Amide derivative (1g) of Ex. 8 | 1.1 |
| Amide derivative (1h) of Ex. 9 | 1.0 |
| Amide derivative (1i) of Ex. 10 | 1.6 |
| Amide derivative (1j) of Ex. 11 | 1.2 |
| Amide derivative (1k) of Ex. 12 | 1.2 |
| Comparative product | 2.3 |

Example 15 (Hair Tonic Formulation)

| (Composition) | (%) |
|---|---|
| (1) Amide derivative obtained in one of Examples 1 to 12 | 1 |
| (2) Aluminum pyrrolidonecarbonate | 0.5 |
| (3) Ethanol | 55.0 |
| (4) Water | Balance |
| (5) Perfume | 0.3 |

(Formulation method)

The amide derivative (1) was dispersed under stirring in water (4), followed by the addition of aluminum pyrrolidonecarbonate (2), ethanol (3) and the perfume (5). The resulting mixture was thoroughly mixed, whereby a suspension-type hair tonic formulation capable of imparting excellent styling and style-retaining properties and good feeling of touch to the hair and also preventing dandruff was obtained.

Example 16 (Hair Rinses)

Hair rinses of the compositions shown in Table 5 were formulated. The touch feeling of the hair after treatment with each hair rinse was ranked by 10 expert panellers in accordance with the ranking standards shown in Table 6. The results are presented in Table 7.

TABLE 5

| | Invention product | Comparative product |
|---|---|---|
| Distearyldimethylammonium chloride | 2 | 2 |
| Propylene glycol | 3 | 3 |
| Amide derivative (1a) obtained in Example 1 | 1 | 1 |
| Perfume | 0.5 | 0.5 |
| Color | Trace | Trace |
| Water | Balance | Balance |

TABLE 6

| Ranking Standards | |
|---|---|
| Feeling of touch | Ranking Score |
| Good | +2 |
| Slightly good | +1 |
| Can't be said good or bad | 0 |
| Slightly bad | −1 |
| Bad | −2 |

TABLE 7

| Evaluated property | Invention product | Comparative product |
|---|---|---|
| Combing smoothness (wet) | +0.5 | 0 |
| Combing smoothness (dry) | +1.4 | −0.2 |
| Dryness and looseness after drying | +1.4 | −0.2 |
| Feeling of touch | +1.3 | −0.3 |

Example 17

External skin care preparations (emulsified cosmetics) of the following composition were formulated to evaluate the compatibility and interaction of the amide derivatives prepared in Examples 1 to 12.

| (Composition) | (%) |
|---|---|
| Amide derivative (1) obtained in one of Examples 1 to 12 | 3.5 |
| Squalane | 2.0 |
| ESTEMOL N-01 | 3.0 |
| RHEODOLE SUPER TW-S120 | 2.1 |
| RHEODOLE SP-S10 | 0.9 |
| EMANONE CH-40 | 1.0 |
| 86% Glycerin | 5.0 |
| Methylparabene | 0.3 |
| Purified water | Balance |

Further, for the sake of comparison, a similar evaluation was conducted with respect to the amide derivative of the following formula (22) disclosed in Example 1 of Japanese Patent Publication No. 42934/1989.

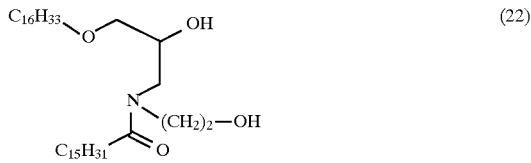
(22)

After each cream so formulated was stored at 5° C. for 4 weeks, i t was observed under polarized light through an optical microscope to determine whether crystallization had taken place or not. As a result, no crystallization was observed on each cream added with the amide derivative according to the present invention but crystallization was observed on the cream added with the above-described amide derivative (22).

Example 18

Bath medicines of the following composition were formulated.

| | (%) |
|---|---|
| Oats extract | 5 |
| Rice germ oil | 10 |
| Amide derivative (1) obtained in one of Examples 1 to 12 | 1 |
| Cholesteryl isostearate | 5 |
| 1-Isostearyl-3-myristoyl glycerol | 10 |
| Octyldodecyl myristate | 30 |
| Liquid paraffin | Balance |
| Polyoxyethylene oleyl ether (12EO) | 10 |
| Polyoxyethylene oleyl ether (4EO) | 6 |
| Methyl paraoxybenzoate | 0.1 |
| Butyl paraoxybenzoate | 0.1 |

We claim:

1. An amide derivative represented by the following formula (1):

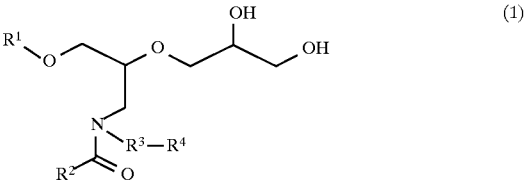
(1)

wherein $R^1$ and $R^2$ may be the same or different and individually represent an optionally-hydroxylated hydrocarbon group having 1 to 40 carbon atoms, $R^3$ represents a linear or branched alkylene group having 1 to 6 carbon atoms or a single bond, and $R^4$ represents a hydrogen atom, a linear or branched alkoxyl group having 1 to 12 carbon atoms or a 2,3-dihydroxypropyloxy group, with the proviso that $R^4$ is a hydrogen atom when $R^3$ is a single bond.

2. An amide derivative according to claim 1, wherein in the formula (1), $R^1$ is a linear or branched alkyl or alkenyl group having 8 to 26 carbon atoms, $R^2$ is a linear or branched alkyl or alkenyl group having 9 to 25 carbon atoms, $R^3$ is a linear alkylene group having 1 to 6 carbon atoms, and $R^4$ is a hydrogen atom, a linear or branched alkoxyl group having 1 to 12 carbon atoms or a 2,3-dihydroxypropyloxy group.

3. An amide derivative according to claim 1, wherein in the formula (1), $R^1$ is a linear or branched alkyl group having 12 to 22 carbon atoms, $R^2$ is a linear or branched alkyl group having 11 to 21 carbon atoms, $R^3$ is a linear alkylene group having 1 to 6 carbon atoms, and $R^4$ is a hydrogen atom, a linear or branched alkoxyl group having 1 to 8 carbon atoms or a 2,3-dihydroxypropyloxy group.

4. An amide derivative according to claim 1, wherein $R^1$ is a hexadecyl group, $R^2$ is a tridecyl group, $R^3$ is a trimethylene group, and $R^4$ is a methoxy group.

5. An external skin care preparation comprising an amide derivative as defined in claim 1.

6. A cosmetic hair care formulation comprising an amide derivative as defined in claim 1.

7. A bath medicine comprising an amide derivative as defined in claim 1.

8. A skin or hair care method comprising applying to the skin or hair a preparation or formulation comprising an amide derivative as defined in claim 1.

9. A bathing method comprising dissolving or dispersing an amide derivative as defined in claim 1 in water and then bathing in the water.

10. An external skin care preparation, a cosmetic hair care formulation or a bath medicine comprising an amide derivative as defined in claim 1.

* * * * *